United States Patent
Li et al.

(10) Patent No.: US 12,364,694 B2
(45) Date of Patent: Jul. 22, 2025

(54) ORGANIC COMPOUNDS

(71) Applicant: INTRA-CELLULAR THERAPIES, INC., New York, NY (US)

(72) Inventors: Peng Li, New Milford, NJ (US); Qiang Zhang, Plainsboro, NJ (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 1076 days.

(21) Appl. No.: 17/040,892

(22) PCT Filed: Mar. 21, 2019

(86) PCT No.: PCT/US2019/023350
§ 371 (c)(1),
(2) Date: Sep. 23, 2020

(87) PCT Pub. No.: WO2019/183341
PCT Pub. Date: Sep. 26, 2019

(65) Prior Publication Data
US 2021/0009592 A1  Jan. 14, 2021

Related U.S. Application Data

(60) Provisional application No. 62/647,488, filed on Mar. 23, 2018.

(51) Int. Cl.
| | | |
|---|---|---|
| *A61K 31/4985* | (2006.01) | |
| *A61K 9/00* | (2006.01) | |
| *A61K 45/06* | (2006.01) | |
| *C07B 59/00* | (2006.01) | |
| *C07D 471/16* | (2006.01) | |

(52) U.S. Cl.
CPC ........ *A61K 31/4985* (2013.01); *A61K 9/0019* (2013.01); *A61K 45/06* (2013.01); *C07B 59/002* (2013.01); *C07D 471/16* (2013.01); *C07B 2200/05* (2013.01)

(58) Field of Classification Search
CPC .. A61K 31/4985; A61K 9/0019; A61K 45/06; C07B 59/002; C07B 2200/05; C07D 471/16; C07D 471/04
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,849,246 A | 7/1989 | Schmidt |
| 4,935,419 A | 6/1990 | Biork et al. |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,629,003 A | 5/1997 | Horstmann et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,847,166 A | 12/1998 | Buchwald et al. |
| 5,902,901 A | 5/1999 | Goodbrand et al. |
| 5,948,430 A | 9/1999 | Zerbe et al. |
| 6,043,370 A | 3/2000 | Kubo et al. |
| 6,166,226 A | 12/2000 | Buchwald et al. |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Alvir et al. Clozapine-Induced Agranulocytosis. The New England Journal of Medicine, 1993, vol. 329, No. 3, pp. 162-167.

Baille, T.A., "The Use of Stable Isotopes in Pharmacological Research," Pharmacol. Reviews, vol. 33, No. 2, pp. 81-132, (1981).

Balbach, S., et al., "Pharmaceutical evaluation of early development candidates 'the 100 mg-approach'", International Journal of Pharmaceutics, vol. 275, p. 1- 12 (2004).

Bastin, R., et al., "Salt Selection and Optimisation Procedures for Pharmaceutical New Chemical Entities", Organic Process and Research Development, vol. 4, No. 5, pp. 427-435 (2000).

Bowman, W.R., et al., "Copper (1) Catalysed Aromatic Nucleophilic Substitution: A Mechanistic and Synthetic Comparison with the SRN 1 Reaction", Tetrahedron Letters, vol. 25(50) p. 5821-5824, (1984).

(Continued)

*Primary Examiner* — Jean P Cornet
(74) *Attorney, Agent, or Firm* — Hoxie & Associates LLC

(57) ABSTRACT

The invention relates to particular deuterated substituted heterocycle fused gamma-carbolines, in free, solid, pharmaceutically acceptable salt and/or substantially pure form as described herein, pharmaceutical compositions thereof, and methods of use in the treatment of diseases involving the 5-HT$_{2A}$ receptor, the serotonin transporter (SERT), pathways involving the dopamine D$_1$ and D$_2$ receptor signaling system, and/or the μ-opioid receptor.

10 Claims, No Drawings

(56) References Cited

U.S. PATENT DOCUMENTS

| | | |
|---|---|---|
| 6,221,335 B1 | 4/2001 | Foster |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,440,710 B1 | 8/2002 | Keinan et al. |
| 6,465,693 B2 | 10/2002 | Buchwald et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,309,772 B2 | 11/2012 | Weiner et al. |
| 8,414,922 B2 | 4/2013 | Bryson et al. |
| 8,461,148 B2 | 6/2013 | Hollander |
| 8,475,793 B2 | 7/2013 | Malefyt |
| 8,598,119 B2 | 12/2013 | Mates et al. |
| 8,603,514 B2 | 12/2013 | Yang et al. |
| 8,648,077 B2 | 2/2014 | Tomesch et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Van over et al. |
| 10,072,010 B2 | 9/2018 | Li et al. |
| 10,077,267 B2 | 9/2018 | Mates et al. |
| 10,117,867 B2 | 11/2018 | Mates et al. |
| 10,118,926 B2 | 11/2018 | Koolman et al. |
| 10,221,176 B2 | 3/2019 | Tomesch et al. |
| 10,245,260 B2 | 4/2019 | Yao et al. |
| 10,322,134 B2 | 6/2019 | Vanover et al. |
| 10,363,220 B2 | 7/2019 | Li |
| 10,464,938 B2 | 11/2019 | Tomesch et al. |
| 10,472,359 B2 | 11/2019 | Li et al. |
| 10,533,015 B1 | 1/2020 | Tusche et al. |
| 10,597,394 B2 | 3/2020 | Mates et al. |
| 10,597,395 B2 | 3/2020 | Tomesch et al. |
| 10,654,854 B2 | 5/2020 | Li et al. |
| 10,682,354 B2 | 6/2020 | Wennogle |
| 10,688,097 B2 | 6/2020 | Yao et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Mates et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 | 6/2021 | Mates et al. |
| 11,052,083 B2 | 7/2021 | Li et al. |
| 11,053,245 B2 | 7/2021 | Mates et al. |
| 11,066,407 B2 | 7/2021 | Tomesch et al. |
| 11,096,944 B2 | 8/2021 | Yao et al. |
| 11,124,514 B2 | 9/2021 | Mates et al. |
| RE48,825 E | 11/2021 | Tomesch et al. |
| RE48,839 E | 12/2021 | Mates et al. |
| 11,311,536 B2 | 4/2022 | Li et al. |
| 11,331,316 B2 | 5/2022 | Li et al. |
| 11,376,249 B2 | 7/2022 | Li et al. |
| 11,407,751 B2 | 8/2022 | Tomesch et al. |
| 11,427,587 B2 | 8/2022 | Li et al. |
| 11,440,911 B2 | 9/2022 | Wennogle et al. |
| 11,453,670 B2 | 9/2022 | Li et al. |
| 11,560,382 B2 | 1/2023 | Mates et al. |
| 11,680,065 B2 | 6/2023 | Li et al. |
| 11,723,909 B2 | 8/2023 | Yao et al. |
| 11,773,095 B2 | 10/2023 | Li et al. |
| 11,806,347 B2 | 11/2023 | Li et al. |
| 11,806,348 B2 | 11/2023 | Li et al. |
| 11,844,757 B2 | 12/2023 | Yao et al. |
| 11,958,852 B2 | 4/2024 | Mates et al. |
| 11,980,617 B2 | 5/2024 | Snyder et al. |
| 12,023,331 B2 | 7/2024 | Snyder et al. |
| 12,070,459 B2 | 8/2024 | Li et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0180875 A1 | 9/2004 | Lee et al. |
| 2004/0186094 A1 | 9/2004 | Robichaud et al. |
| 2004/0209864 A1 | 10/2004 | Robichaud et al. |
| 2004/0220178 A1 | 11/2004 | Robichaud et al. |
| 2005/0127482 A1 | 6/2005 | Fauty et al. |
| 2005/0166771 A1 | 8/2005 | Gygi et al. |
| 2005/0222209 A1 | 10/2005 | Zeldis et al. |
| 2005/0239768 A1 | 10/2005 | Lee et al. |
| 2006/0128713 A1 | 6/2006 | Jolidon et al. |
| 2006/0148808 A1 | 7/2006 | Robichaud et al. |
| 2006/0178362 A1 | 8/2006 | Robichaud et al. |
| 2006/0205787 A1 | 9/2006 | Muller et al. |
| 2007/0066677 A1 | 3/2007 | Igo et al. |
| 2007/0082929 A1 | 4/2007 | Gant et al. |
| 2007/0197695 A1 | 8/2007 | Potyen et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0280941 A1 | 11/2008 | Lourtie et al. |
| 2008/0287450 A1 | 11/2008 | Cid-Nunez et al. |
| 2009/0076159 A1 | 3/2009 | Czarnik |
| 2009/0202631 A1 | 8/2009 | Yam et al. |

(56) References Cited

U.S. PATENT DOCUMENTS

| | | |
|---|---|---|
| 2009/0209608 A1 | 8/2009 | Czarnik |
| 2010/0113781 A1 | 5/2010 | Tomesch et al. |
| 2010/0159033 A1 | 6/2010 | Gant et al. |
| 2010/0298382 A1 | 11/2010 | Seeman |
| 2011/0071080 A1 | 3/2011 | Mates et al. |
| 2011/0112105 A1 | 5/2011 | Tomesch et al. |
| 2011/0263592 A1 | 10/2011 | Xiong et al. |
| 2012/0157469 A1 | 6/2012 | Surman et al. |
| 2012/0196814 A1 | 8/2012 | Gong et al. |
| 2013/0202692 A1 | 8/2013 | Mates et al. |
| 2014/0050783 A1 | 2/2014 | Mates et al. |
| 2014/0080816 A1 | 3/2014 | Koolman et al. |
| 2014/0323491 A1 | 10/2014 | Tomesch et al. |
| 2014/0364609 A1 | 12/2014 | Tomesch et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0166540 A1 | 6/2015 | Mates et al. |
| 2015/0166542 A1 | 6/2015 | Kier-Nielsen |
| 2016/0031885 A1 | 2/2016 | Li et al. |
| 2016/0330425 A1 | 2/2016 | Mates et al. |
| 2016/0159787 A1 | 6/2016 | Linz et al. |
| 2016/0194325 A1 | 7/2016 | Tomesch et al. |
| 2016/0194326 A1 | 7/2016 | Tomesch et al. |
| 2016/0310502 A1 | 10/2016 | Van over et al. |
| 2016/0354315 A1 | 12/2016 | Li |
| 2017/0037048 A1 | 2/2017 | Mates et al. |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0283417 A1 | 10/2017 | Li et al. |
| 2017/0319580 A1* | 11/2017 | Yao .................... A61K 31/445 |
| 2018/0044337 A1 | 2/2018 | Tomesch et al. |
| 2018/0200256 A1 | 7/2018 | Van over et al. |
| 2019/0330211 A1 | 10/2019 | Li et al. |
| 2020/0017499 A1 | 1/2020 | Mates et al. |
| 2020/0247806 A1 | 8/2020 | Mates et al. |
| 2020/0392135 A1 | 12/2020 | Wennogle et al. |
| 2020/0407362 A1 | 12/2020 | Mates et al. |
| 2021/0002280 A1 | 1/2021 | Mates et al. |
| 2021/0008065 A1 | 1/2021 | Li et al. |
| 2021/0093634 A1 | 4/2021 | Snyder et al. |
| 2021/0163481 A1 | 6/2021 | Li et al. |
| 2022/0048910 A1 | 2/2022 | Li et al. |
| 2022/0056030 A1 | 2/2022 | Li et al. |
| 2022/0056031 A1 | 2/2022 | Li et al. |
| 2022/0160704 A2 | 5/2022 | Torralva |
| 2022/0184072 A1 | 6/2022 | Davis et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 564 671 | 1/2005 |
| EP | 1 539 115 | 6/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2006/034187 | 3/2006 |
| WO | WO 2006/081251 | 8/2006 |
| WO | WO 2007/025103 | 3/2007 |
| WO | WO 2007/084841 | 7/2007 |
| WO | WO 2009/017836 | 2/2009 |
| WO | WO 2015/154030 | 10/2015 |
| WO | WO 2015/191554 | 12/2015 |
| WO | WO 2017/117514 | 7/2017 |
| WO | WO-2017117514 A1 * | 7/2017 ........... A61K 31/437 |
| WO | WO 2017/165755 | 9/2017 |

OTHER PUBLICATIONS

Bowman, W.R., et al., "Intramolecular Aromatic Substitution (SRNI) Reactions—Use of Entrainment for the Preparation of Benzothiazoles," Tetrahedron Letters, vol. 23, pp. 5093-5096, (1982).

Bowman, W.R., et al.,"Synthesis of IH-quinazoline-4-ones using intramolecular aromatic nucelophilic substitution," Arkivoc, vol. x, pp. 434-442 (2003).

Browne, T.R., "Stable Isotope Techniques in Early Drug Development: An Economic Evaluation," J. Clin. Pharmacol., vol. 38, pp. 213-220, (1998).

Byrn, S., et al., "Pharmaceutical Solids: A Strategic Approach to Regulatory Considerations", Pharmaceutical Research, vol. 12, No. 7, p. 945-954 (1995).

Caira, et al., "Crystalline Polymorphism of Organic Compounds," Topics in Current Chemistry, vol. 198, p. 163-203, (1998).

Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).

Crawford, K., et al., "Copper-Catalyzed amidations of bromo substituted furans and thiophenes", Tetrahedron Letters, vol. 43, p. 7365-7368, (2002).

Darmani, N. A., et al., "Do Functional Relationships Exist Between 5-HT IA and 5-HT2 Receptors?" Pharmacology and Biochemistry & Behavior, vol. 36, p. 901-906, (1990).

Davis et al. "ITI-007 demonstrates brain occupancy at serotonin 5-HT2A and dopamine D2 receptors and serotonin transporters using positron emission tomography in healthy volunteers," Psychopharmacology, Published Online Apr. 7, 2015, vol. 232, pp. 2863-2872.

Davis et al. "ITI-007 in the treatment of schizophrenia: from novel pharmacology to clinical outcomes," Expert Review of Neurotherapeutics, vol. 16, No. 6, pp. 601-614 (2016).

Dyck, L.E., et al., "Effects of Deuterium Substitution on the Catabolism of—Phenylethylamine: An In Vivo Study," Journal of Neurochemistry, vol. 46, Issue 2, pp. 399-404, (1986).

Evindar, G., et al., "Copper- and Palladium-Catalyzed Intramolecular Aryl Guanidinylation: An Efficient Method for the Synthesis of 2-Aminobenzimidazoles", Organic Letters, vol. 5, No. 2, p. 133-136, (2003).

Fawcett, J., "Posttraumatic Stress Disorder, Stress, and Happiness", Psychiatric Annals Journal, vol. 28, Issue 8, p. 427-428, (1998).

Fee, W.W., et al., "Copper (11)-promoted solvolyses of nickel (II) complexes III. Tetradentate Schiff base ligands containing various diamine segments," Aust. J. Chem., vol. 26, pp. 1475-1485, (1973).

Ferreira, I., et al., "Novel synthetic routes to thienocarbazoles via palladium or copper catalyzed amination or amidation of arylhalides and intramolecular cyclization", Tetrahedron, vol. 58, p. 7943-7949, (2002).

Foster, A.B., "Deuterium Isotope Effects in the Metabolism of Drugs and Xenobiotics: Implications for Drug Design," 1985, Advances in Drug Research, vol. 14, pp. 1-40.

Friedman, M.J .. , "Current and Future Drug Treatment for Posttraumatic Stress Disorder Patients", Psychiatric Annals Journal, vol. 28, Issue 8, p. 464-468, (1998).

Goodbrand, H.B., et al., "Ligand-Accelerated catalysis of the Ullmann condensation: Application to hole conducting triarylamines," J. Org. Chem., vol. 64, pp. 670-674, (1999).

Gouyette, A., "Synthesis of Deuterium-labelled Elliptinium and its Use in Metabolic Studies," Biomedical and Environmental Mass Spectrometry, vol. 15, pp. 243-247, (1988).

(56) References Cited

OTHER PUBLICATIONS

Guillory, J.K., "Generation of Polymorphs, Hydrates, Solvates, and Amorphous Solids", Polymorphism in Pharmaceutical Solids, Chapter 5, p. 183-226 (1999).
Hackam, D., et al., "Translation of Research Evidence from Animals to Humans", JAMA, vol. 296(14), p. 1731-1732 (2006).
Hamann, B., et al., "Systematic Variation of Bidentate Ligands used in Aryl Halide Amination. Unexpected Effects of Steric, Electronic, and Geometric Perturbations", J. Am. Chem. Soc., vol. 120, p. 3694-3703, (1998).
Harbert, C.A. et al., "Neuroleptic Activity in 5-Aryltetrahydro-y-carbolines", J. Med. Chem., vol. 23, pp. 635-643 (1980).
Hartwig, J., "Palladium-catalyzed amination of aryl halides: Mechanism and rational catalyst design," Synlett, pp. 329-340, (1996).
Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).
Haskins, N.J., "The Application of Stable Isotopes in Biomedical Research," Biological Mass Spectrometry, vol. 9, No. 7, pp. 269-277, (1982).
Hassan, J., et al., "Aryl-aryl bond formation one century after the discovery of the ullmann reaction," Chem. Rev., vol. 102, pp. 1359-1469, (2002).
Honma, S., et al., "The Metabolism of Roxatidine Acetate Hydrochloride: Liberation of Deuterium from the Piperidine Ring during Hydroxylation," Drug Metabolism and Disposition, vol. 15, No. 4, p. 551, (1987).
International Search Report for International Patent Application PCT/US2015/24340, prepared by the International Search Authority, date mailed Jun. 25, 2015, 2 pages.
International Search Report issued in International Application No. PCT/US2008/003340, mailed Aug. 8, 2008, 3 pages.
International Search Report issued in International Application No. PCT/US2017/015178, mailed Apr. 12, 2017, 3 pages.
International Search Report issued in International Application No. PCT/US2018/043100, mailed Oct. 2, 2018, 2 pages.
Ito, T., et al., "Studies of organic catalytic reactions. VI. The function of pyridine and copper in the Rosenmund-von Braun reaction," Bulletin of the Chemical Society of Japan vol. 41, pp. 419-423, (1968).
Ji, J., et al., "Selective amination of polyhalopyridines catalyzed by a palladium-xantphos complex," Organic Letters, vol. 5, No. 24, pp. 4611-4614, (2003).
Kametani, T., et al., "A Novel Synthesis of Indole Derivatives", Heterocycles, vol. 14 (3), p. 277-280, (1980).
Kang, S-K., et al., "Copper-catalyzed N-arylation of aryl iodides with benzamides or nitrogen heterocycles in the presence of ethylendiamine," Synlett, No. 3, pp. 427-430, (2002).
Kay, S.R., et al., "The Positive and Negative Syndrome Scale (PANSS) for Schizophrenia," Schizophrenia Bulletin, vol. 13, Issue 2, pp. 261-276, (1987).
Kessler, RC., et al., "Lifetime Prevalence and Age-of-Onset Distributions of DSM-IV Disorders in the National Comorbidity Survey Replication," Arch Gen Psychiatry; vol. 62, pp. 593-602, (2005).
Khorana, N., et al., "Gamma-Carbolines: Binding at 5-HT5A Serotonin Receptors," Bioorganic & Medicinal Chemistry, vol. 11, Issue 5, 6, pp. 717-722, p. 718 Table 1, (2003).
Kiyomori, A., et al., "An efficient copper-catalyzed coupling of aryl halides with imidazoles," Tetrahedron Letters, vol. 40, pp. 2657-2660, (1999).
Klapars, A., et al., "A general and efficient copper catalyst for the amidation of aryl halides and the N-arylation of nitrogen heterocycles," J. Am. Chem. Soc., vol. 123, No. 25, pp. 7727-7729, (2001).
Klapars, A., et al., "A general and efficient copper catalyst for the amidation of aryl halides," J. Am. Chem. Soc., vol. 124, pp. 7421-7428, (2002).
Kondratov, S.A., et al., "Nucelophilic substitution in the aromatic series. Lv. Reaction of o-nitrochlorobenzene with ammonia in the presence of copper compounds," Zhurnal Organidreskoi Khimii, vol. 51(11), pp. 2387-2390, (1979).
Kwong, F.Y., et al., "Mild and efficient copper-catalyzed amination of aryl bromides with primary alkylamines," Organic Letters, vol. 5, No. 6, pp. 793-796, (2003).
Lee, T., et al. "Novel, Highly Potent, Selective 5-HT2AID2 Receptor Antagonists as Potential Atypical Antipsychotics," Bioorg. Med. Chem. Lett., vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, vol. 57, p. 2670-2682 (2014).
Lieberman, J.A., et al., "ITI-007 for the Treatment of Schizophrenia: A 4-Week Randomized, Double-Blind, Controlled Trial," Biol. Psychiatry, 79(12), pp. 952-961, (2015).
Lopez, et al., "Psychiatric Symptoms Vary with the Severity of Dementia in Probably Alzheimer's Disease," J. Neuropsychiatry Clin. Neurosc., vol. 15(3), pp. 346-353, (2003).
Louie, J., et al., "Palladium-Catalyzed Synthesis of Arylamines from Aryl Halides, Mechanistic Studies lead to Coupling in the Absence of Tin Reagents," Tetrahedron Letters, vol. 36(21), p. 3609-3612, (1995).
Lounkine, E., et al., "Formal Concept Analysis for the Identification of Molecular Fragment Combinations Specific for Active and Highly Potent Compounds," J. Med. Chem., vol. 51, No. (17), 5342-5348, (2008).
Marcoux, J-F., et al., "A general copper-catalyzed synthesis of diaryl ethers," J. Am. Chem. Soc., vol. 119, pp. 10539-10540, (1997).
Marek, G.J., et al., "Synergistic Action of 5-HT2A Antagonists and Selective Serotonin Reuptake Inhibitors in Neuropsychiatric Disorder," Neuropsychopharmacology, (2003), vol. 28, pp. 402-412.
Mulrooney, C., et al., "Recent developments in copper-catalyzed n-arylation with aryl halides," Essay—University of Pennsylvania (2004).
Murakami et al., "Fischer Indolization of Ethyl Pyruvate 2-[2-(Trifluoromethyl) phenyl]-phenylhydrazone and New Insight into the Mechanism of the Goldberg Reaction." Chem. Pharm. Bull, vol. 43(8), p. 1281-1286, (1995).
Nagai, Y., et al., "Synthesis of 2,3,4,4a,5,9b-hexahydro-1H-pyrido[4,3-b] indole derivatives and their central nervous system activities." Journal of Medicinal Chemistry, vol. 22, No. 6, p. 677-683. 1979.
Perlis, R.H., et al., "Clinical Features of Bipolar Depression Versus Major Depressive Disorder in Large Multicenter Trials," Am J Psychiatry, vol. 163, (2006), pp. 225-231.
Pieniaszek, H.J., et al., "Moricizine Bioavailability via Simultaneous Dual, Stable Isotope Administration: Bioequivalence Implications," J. Clin. Pharmacol., vol. 39, pp. 817-825, (1999).
Pubchem, CID-22036753, p. 4, pp. 1-12 (2007).
Pubchem, CID-9953107, p. 3, pp. 1-9 (2006).
PubChem, Open Chemistry Database, Compound Summary for CID-22036753, pp. 4, (2007), 12 pages.
PubChem, Open Chemistry Database, Compound Summary for SID 103920954 (2011) 6 pages.
Rackova, L., et al., "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548, (2006).
Rainer, M.K., "Risperidone long-acting injection: a review of its long term safety and efficacy," Neuropsychiatric Disease and Treatment, vol. 4, No. 5, pp. 919-927 (2008).
Ramaswamy, et al., "Failed Efficacy of Ziprasidone in the Treatment of Post-Traumatic Stress Disorder," Contemporary Clinical Trials Communications, vol. 2, pp. 1-5, (2016).
Renner, J.A., Jr., "Management of Psychiatric Medications in Patients Receiving Buprenorphine/Naloxone," PCSS MAT Training Providers' Clinical Support System for Medical Assisted Treatment, Last Updated: Nov. 28, 2013, 4 pages.
Sadighi, J.P., et al., "A highly active palladium catalyst system for the arylation of anilines," Tetrahedron Letters, vol. 39, pp. 5327-5330, (1998).
Savjani, K., et al., "Drug Solubility: Importance and Enhancement Techniques," International Scholarly Research Network Pharmaceutics, vol. 2012, pp. 1-10, (2012).

(56) References Cited

OTHER PUBLICATIONS

Semla, et al., "Off-Label Prescribing of Second-Generation Antipsychotics to Elderly Veterans with Posttraumatic Stress Disorder and Dementia," J. Am. Geriatr. Soc., vol. 65, pp. 1789-1795, (2017); DOI: 10.1111/iirs.14897.
Singhal, D., et al., "Drug polymorphism and dosage form design: a practical perspective", Advanced Drug Delivery Reviews, vol. 56, pp. 335-347 (2004).
Snyder, G.L., et al., "Functional profile of a novel modulator of serotonin, dopamine, and glutamate neurotransmission," Psychopharmacology, vol. 232, p. 605-621 (2015) Published online Aug. 2014, DOI 10.1007/s00213-014-3704-1.
Southwick, S.M., et al., "Neuroendocrine Alterations in Posttraumatic Stress Disorder," Psychiatric Annals Journal, vol. 28, Issue 8, p. 436-442, (1998).
Sugahara, M., et al., "A Facile Copper-Catalyzed Ullman Condensation: N-Arylation of Heterocyclic Compounds Containing an—NHCO—Moiety", Chem. Pharm. Bull., vol. 45, No. 4, p. 719-721, (1997).
Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).
Tung, R., "The Development of Deuterium-Containing Drugs," Innovations in Pharmaceutical Technoloirv, vol. 32, (2010), pp. 1-4.
Wagaw, S., et al., "A palladium-catalyzed method for the preparation of indoles via the Fischer in dole synthesis," Journal of the American Chemical Society, vol. 121, No. 44, pp. 10251-10263, (1999).
Wolen, R. L., "The Application of Stable Isotopes to Studies of Drug Bioavailability and Bioequivalence," J. Clin. Pharmacol., vol. 26, pp. 419-424, (1986).
Wolfe, J.P., et al., "An improved catalyst system for aromatic carbon-nitrogen bond formation: The possible involvement of bis(phosphine) palladium complexes as key intermediates," JACS, vol. 118, pp. 7215-7216, (1996).
Wolfe, J.P., et al., "Intramolecular palladium-catalyzed aryl amination and aryl amidation," Tetrahedron, vol. 52, No. 21, pp. 7525-7546, (1996).
Wolter, M., et al., "Synthesis ofN-aryl hydrazides by copper-catalyzed coupling of hydrazides with aryl iodides," Organic Letters, vol. 3, No. 23, pp. 3803-3805, (2001).
Yamada, K., et al., "A mild copper-mediated intramolecular amination of aryl halides," Synlett, No. 2, oo. 231-234, (2002).
Yang, B.H., "The development of efficient protocols for the palladium-catalyzed cyclization reactions of secondary amides and carbamates," Organic Letters, vol. 1, No. 1, pp. 35-37, (1999).
Zhang, Z., et al., "Highly efficient copper-catalyzed N-arylation of alkylamines with aryl iodides using phosphoramidite as ligand," Catalysis Communications, vol. 6, p. 784-787, (2005).
Baba et al., "Studies on drug metabolism by use of isotopes. 23. Metabolic study of 1-butyryl-4-cinnamylpiperazine in the rat during development of tolerance by using two kinds of deuterium-labeled forms", J. Med. Chem., 21(6), pp. 525-529, (1978).
Kudla, et al., "Influence of G protein-biased agonists of µ-opioid receptor on addiction-related behaviors," Pharmacol Rep., 73(4), pp. 1033-1051, (2021).
Torralva, et al., "Fentanyl but not Morphine Interacts with Nonopioid Recombinant Human Neurotransmitter Receptors and Transporters," J Pharmacol Exp Ther., 374(3), pp. 376-391, (2020).
Centers for Disease Control and Prevention [Online]. "Prevent Opioid Use Disorder". [Retrieved Dec. 9, 2021]. Retrieved from the Internet: <URL: https://www.cdc.gov/opioids/overdoseprevention/opioid-use-disorder.html>. Published Oct. 11, 2017. One Page . (Year: 2017).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Helfer et al., "Efficacy and Safety of Antidepressants Added to Antipsychotics for Schizophrenia: A Systematic Review and Meta-Analysis," Am. J. Psychiatry, 173(9):876-886 (2016).
Howes et al., "Glutamate and dopamine in schizophrenia: An update for the 21st century", J. Psychopharmacol., 29(2): 97-115 (2015).
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
Kendrick, "The newer, 'atypical' antipsychotic drugs—their development and current therapeutic use", British J. General Practice, 49: 745-749 (1999).
Makadia et al., "Poly Lactic-co-Glycolic Acid (PLGA) as Biodegradable Controlled Drug Delivery Carrier," Polymers (Basel), vol. 3, No. 3, pp. 1377-1397, (2011).
Möller and P Czobor, "Pharmacological Treatment of Negative Symptoms in Schizophrenia," Eur. Arch. Psychiatry Clin. Neurosci., 265: 567-578 (2015).
Sullivan, et al., "Exploring Opioid-Sparing Multimodal Analgesia Options in Trauma: A Nursing Perspective", Journal of Trauma Nursing, 23(6), pp. 361-375, (2016).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, K., et al., "ITI-007: A Novel Therapy for the Treatment of Schizophrenia and Related Psychoses," International Clinical Psychopharamcology, vol. 26, e56, 1 page, (2011).
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Calabrese, J. et al., "Efficacy and Safety of Lumateperone for Major Depressive Episodes Associated with Bipolar I or Bipolar II Disorder: A Phase 3 Randomized Placebo-Controlled Trial," American Journal of Psychiatry, vol. 178, No. 12, pp. 1098-1106, (2021), published online Sep. 23, 2021, DOI: https://doi.org/10.1176/appi.aip.2021.20091339.
Correll, C. et al., "Efficacy and Safety of Lumateperone for Treatment of Schizophrenia a Randomized Clinical Trial," JAMA Psychiatry, vol. 77, No. 4, pp. 349-358, (2020).
Davis, R. et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis, R. et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Davis, R. et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary p. 93).
Edinoff, A. et al., "Lumateperone for the Treatment of Schizophrenia," Psychopharmacology Bulletin, vol. 50, No. 4, pp. 32-59, (2020).
Harvey, P. et al., "Lumateperone Improves Negative Symptoms Related to Emotional Experience (Avolition) in Patient with Schizophrenia," Abstract presented at the American Society of Clinical Psychopharmacology (ASCP) Annual Meeting: May 29-Jun. 1, 2018: Miami, FL.
Hlavinka, E., "Schizophrenia Tx Eases Depression in Bipolar Disorder: Lumateperone Offers Greater Rate of Response, Remis-

(56) References Cited

OTHER PUBLICATIONS sion versus Placebo," Medpage Today, 7 pages, (2020); https://www.medpagetoday.com/meetingcoverage/psychcongress/88584.

Kumar, B. et al., "Lumateperone: A New Treatment Approach for Neuropsychiatric Disorders," Drugs of Today, vol. 54, No. 12, pp. 713-719, (2018).

Longo, G. et al., "The Novel Antipsychotic Lumateperone (Iti-007) in the Treatment of Schizophrenia: A Systematic Review," Brain Sciences, vol. 13, No. 12, 18 pages, (2023).

Managing Depressive Symptoms in Substance Abuse Clients During Early Recovery [Internet]. Rockville (MD): Substance Abuse and Mental Health Services Administration (US); 2008. (Treatment Improvement Protocol (TIP) Series, No. 48.) Appendix D-DSM-IV-TR Mood Disorders.

Noble, F. et al., "The opioid receptors as targets for drug abuse medication," British Journal of Psychology, vol. 172, pp. 3964-3979, (2015).

O'Gorman, et al., "Lumateperone (ITI-007): A Novel Investigational Agent with Broad Therapeutic Potential Across Multiple Neuropsychiatric Disorders," Poster p. 1.g.038, European College of Neuropsychopharmacology (ECNP) Congress (2017).

Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.

Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.

Press Release, "Intra-Cellular Therapies Announces Additional Results From Phase I/II Clinical Trial for ITI-007 in Healthy Geriatric Subjects and Patients With Dementia," Intra-Cellular Therapies, Press Release Date: Nov. 21, 2014.

Press Release, "Intra-Cellular Therapies Announces Top-Line Results from the Second Phase 3 Trial of ITI-007 in Patients with Schizophrenia (Study '302)", Intra-Cellular Therapies, Press Release Date: Sep. 28, 2016, 8 pages, available at: https://globenewswire.com/news-release/2016/09/28/875435/0/en/Intra-Cellular-Therapies-Announces-Top-Line-Results-from-the-Second-Phase-3-Trial-of-ITI-007-in-Patients-with-Schizophrenia-Study-302.html.

Press Release, "Intra-Cellular Therapies Reports Positive Final Results of a Phase II Clinical Trial With ITI-007 in Patients with Sleep Maintenance Insomnia.", Intra-Cellular Therapies, Press Release Date: Mar. 10, 2009, 3 pages, available at: https://ir.intracellulartherapies.com/static-files/375e1667-6457-4cd9-95dc-616ca3b5d02b.

Satlin, A. et al., "ITI-007 (Lumateperone) for the Treatment of Agitation in Patients with Dementia, including Alzheimer's Disease," Alzheimer's & Dementia, vol. 14, No. 7, pp. 678-679, (2018), (Alzheimer's Assoc. International Conference 2018, summary of Poster p. 2-032).

Satlin, A. et al., "ITI-007 (Lumateperone) for the Treatment of Agitation in Patients with Dementia, including Alzheimer's Disease," Poster p. 2-032, Alzheimer's Assoc. International Conference 2018, (2018).

Vanover, K. et al., "Dopamine D2 receptor occupancy of lumateperone (ITI-007): a Positron Emission Tomography Study in patients with schizophrenia," Neuropsychopharmacology, vol. 44, pp. 598-605, (2019).

Vanover, K. et al., "Lumateperone (ITI-007): A Novel Investigational Agent with Broad Therapeutic Potential Across Multiple Neuropsychiatric Disorders," European Neuropsychopharmacology, vol. 27, pp. S660-S661 (2017) (Summary of ECNP Poster p. 1.g.038).

Vanover, K. et al., Abstracts of the 13th International Congress on Schizophrenia (ICOSR) (Apr. 2-6, 2011), Schizophrenia Bull., vol. 37, Suppl. 1., p. 325, (2011).

Volcow, N. et al., "Opioid Abuse in Chronic Pain—Misconceptions and Mitigation Strategies," The New England Journal of Medicine, vol. 374, No. 13, pp. 1253-1263, (2016).

* cited by examiner

ORGANIC COMPOUNDS

CROSS-REFERENCE TO RELATED APPLICATIONS

This application is a U.S. National Stage application under 35 U.S.C. § 371 of International Application No. PCT/US2019/023350, filed on Mar. 21, 2019, which claims priority to and the benefit of U.S. Provisional Application No. 62/647,488, filed on Mar. 23, 2018, the contents of each of which are hereby incorporated by reference in their entireties.

FIELD OF THE INVENTION

The invention relates to particular deuterated substituted heterocycle fused gamma-carbolines, in free, solid, pharmaceutically acceptable salt and/or substantially pure form as described herein, pharmaceutical compositions thereof, and methods of use in the treatment of diseases involving the 5-$HT_{2A}$ receptor, the serotonin transporter (SERT), pathways involving dopamine $D_1$ and/or $D_2$ receptor signaling systems, and/or the μ-opioid receptor, e.g., diseases or disorders such as anxiety, psychosis, schizophrenia, sleep disorders, sexual disorders, migraine, conditions associated with pain (including cephalic pain, neuropathic pain, and as an acute analgesic), fibromyalgia, chronic fatigue, social phobias, gastrointestinal disorders such as dysfunction of the gastrointestinal tract motility and obesity; depression and mood disorders, such as those associated with psychosis or Parkinson's disease; psychosis such as schizophrenia associated with depression; bipolar disorder; drug dependencies, such as opiate dependency and alcohol dependency, drug withdrawal symptoms; obsessive-compulsive disorder (OCD), obsessive-compulsive personality disorder (OCPD), and related disorders; and other psychiatric and neurological conditions, as well as to combinations with other agents. In some embodiments, the disease or disorders may include treatment-resistant depression, cocaine dependency, and/or amphetamine dependency.

BACKGROUND OF THE INVENTION

Substituted heterocycle fused gamma-carbolines are known to be agonists or antagonists of 5-$HT_2$ receptors, particularly 5-$HT_{2A}$ receptor, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. U.S. Patent Publications 2010/113781 and 2004/209864 also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, US 2011/071080 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects associated with high occupancy of the dopamine $D_2$ pathways or side effects of other pathways (e.g., $GABA_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. US 2011/112105 also discloses of methods of preparing toluenesulfonic acid addition salt crystals of these substituted heterocycle fused gamma-carbolines.

The related publications WO 2017/132408 and US 2017/319586 disclose novel oxo-metabolites of the compounds disclosed in the above-mentioned publications. These new oxo-metabolites retain much of the unique pharmacologic activity of the parent compounds, including serotonin receptor inhibition, SERT inhibition, and dopamine receptor modulation. However, these oxo-metabolites were found to unexpectedly also show significant activity at mu-opiate receptors.

Obsessive-compulsive disorder (OCD) and related disorders, have become highly prevalent and are difficult to treat. OCD is estimated to affect about 2.3% of people at some point in their lives, and during a given year, it is estimated than 1.2% of people worldwide suffer from the disorder. Half of people who suffer from OCD begin to show symptoms before the age of 20, which can seriously affect their ability to obtain an adequate and effective education. Without effective treatment, however, the disease can last for decades. The mainstay of pharmacologic OCD treatment is with selective serotonin reuptake inhibitors (SSRIs). A second line of therapy is with antipsychotic agents, such as clomipramine, risperidone, quetiapine and olanzapine. A significant number of patients either do not respond to these agents or cannot handle the side effects caused by these agents. More recently, it has been reported that the opioid analgesic tramadol may be effective in treating OCD. Opiates operate by an entirely different pathway from traditional OCD treatment agents, so they offer the possibility of treatment for people who cannot take the traditional serotonergic agents or for whom these agents are ineffective. However, strong opiate agents can be addictive, and their use may be contraindicated in some patients. There thus remains an urgent need for new treatments for OCD and related disorders.

SUMMARY OF THE INVENTION

Compounds of Formula A and B, shown below, are a potent serotonin 5-$HT_{2A}$ receptor antagonists and mu-opiate receptor partial agonists. These compounds also interact with dopamine receptors, particular the dopamine D1 receptors.

Formula A

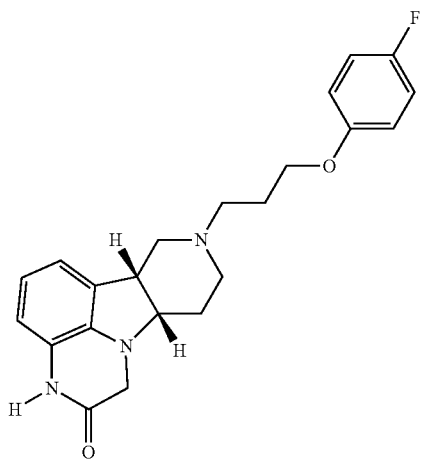

Formula B

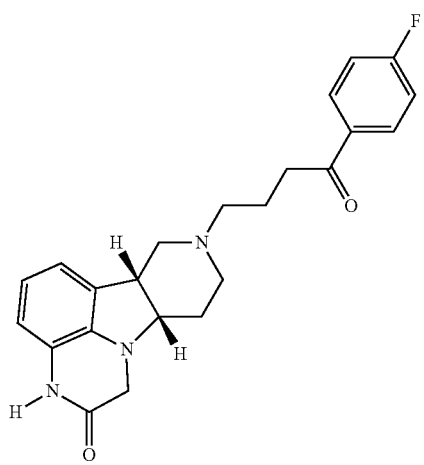

The Compounds of Formula A and B and their analogs are useful for the treatment or prophylaxis of central nervous system disorders, but there is a need in the art for analogs, such as isotopic analogs, of the Compounds of Formula A and B that when administered to a patient can provide for improved therapeutic concentrations or improved pharmacokinetic distribution or dynamics of these compounds. The present disclosure fills this need by providing Compounds of Formula I and II, et seq., which are deuterated analogs of the Compounds of Formula A and B. Due to their useful metabolic and pharmacokinetic profile, the Compounds of the present disclosure may be particularly suited for formulation as long-acting or extended-release compositions that when administered to a patient can provide for improved therapeutic amounts concentrations of the compounds A and B and their analogs over an extended period of time.

In a first aspect, the present disclosure relates to a compound (Compound I) of Formula I:

Formula I

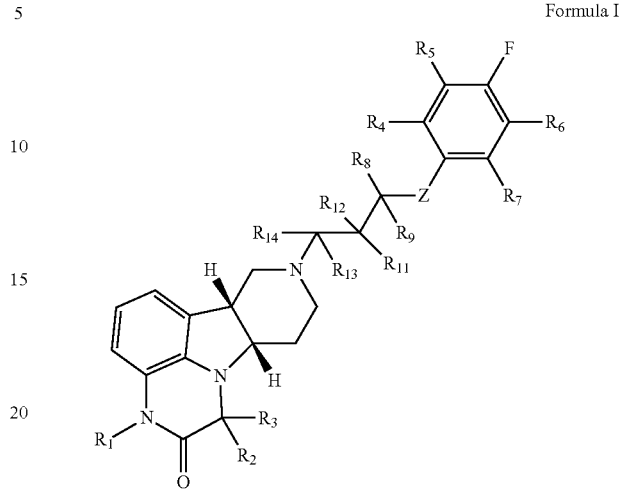

wherein:
$R^1$ is H or $C_{1-4}$ alkyl (e.g., methyl);
Z is O, or —C(O)—;
$R^2$ and $R^3$ are each independently selected from H and D (deuterium); and
each of $R^4$ to $R^{14}$ is independently selected from H and D;
in free or salt form, for example in an isolated or purified free or salt form,
provided that at least one of $R^2$ to $R^{14}$ is D.

The present disclosure provides additional exemplary embodiments of the Compound of Formula I, in free or salt form, for example in an isolated or purified free or salt form, including:

1.1 Compound I, wherein Z is O;
1.2 Compound I, wherein Z is —C(O);
1.3 Compound I, 1.1, or 1.2, wherein $R^1$ is methyl;
1.4 Any of Compounds 1.1-1.3, wherein $R^2$ is H and $R^3$ is D;
1.5 Any of Compounds 1.1-1.3, wherein $R^2$ is D and $R^3$ is D;
1.6 Any of Compounds 1.1-1.3, wherein $R^2$ is H and $R^3$ is H;
1.7 Any of Compounds 1.1-1.6, wherein any one of $R^4$ to $R^7$ is D;
1.8 Any of Compounds 1.1-1.6, wherein any two of $R^4$ to $R^7$ are D;
1.9 Any of Compounds 1.1-1.6, wherein any three of $R^4$ to $R^7$ are D;
1.10 Any of Compounds 1.1-1.6, wherein all four of $R^4$ to $R^7$ are D;
1.11 Any of Compounds 1.1-1.10, wherein all six of $R^8$ to $R^{14}$ are H;
1.12 Any of Compounds 1.1-1.10, wherein any one or two of $R^8$ to $R^{14}$ are D;
1.13 Any of Compounds 1.1-1.10, wherein any three or four of $R^8$ to $R^{14}$ are D;
1.14 Any of Compounds 1.1-1.10, wherein any five or six of $R^8$ to $R^{14}$ are D;
1.15 Any of Compounds 1.1-1.10, wherein all six of $R^8$ to $R^{14}$ are D;
1.16 Compound I, or any of 1.1-1.15, in free form;
1.17 Compound I, or any of 1.1-1.15 in salt form, e.g., pharmaceutically acceptable salt form;

1.18 Compound I or any of 1.1-1.15 in solid form;

1.19 Compound I or any of 1.1-1.18, in substantially pure diastereomeric form (i.e., substantially free from other diastereomers);

1.20 Compound I or any of 1.1-1.18 having a diastereomeric excess of greater than 70%, preferably greater than 80%, more preferably greater than 90% and most preferably greater than 95%.

1.21 Compound I or any of 1.1-1.20, having greater than 50% incorporation of deuterium at one or more of the indicated positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

1.22 Compound I or any of 1.1-1.21 in isolated or purified form.

1.23 Compound I or any of 1.1-1.22, wherein the compound is selected from the group consisting of:

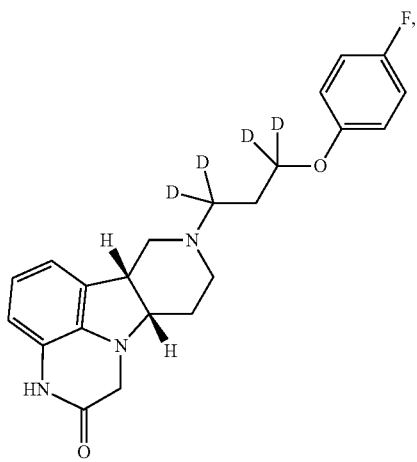

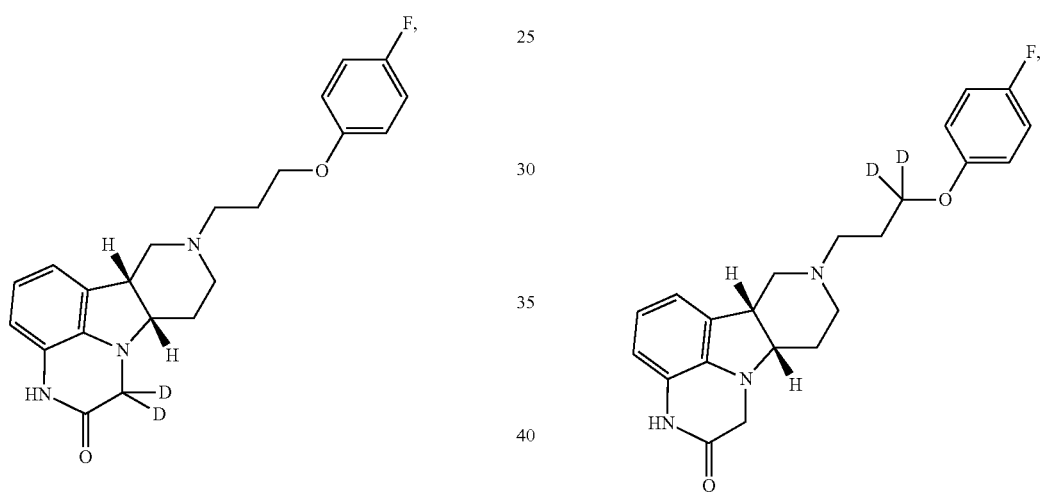

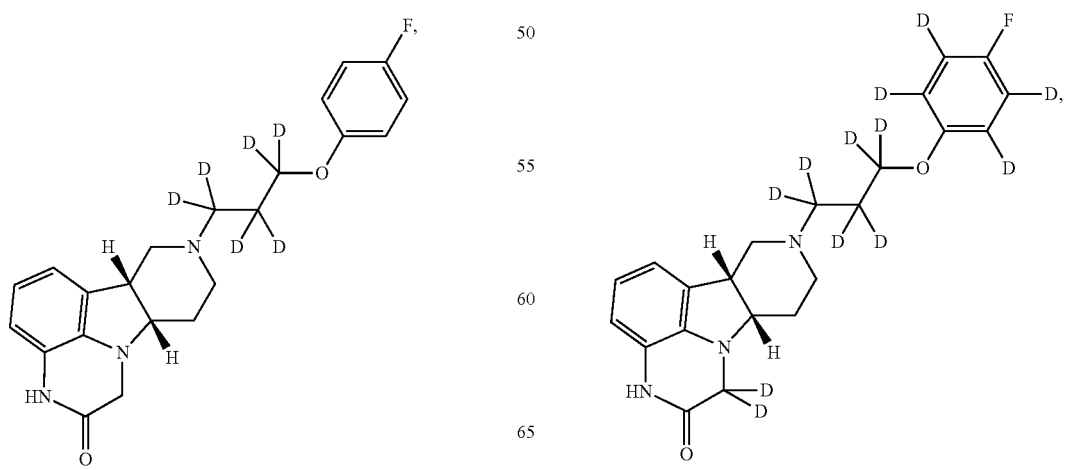

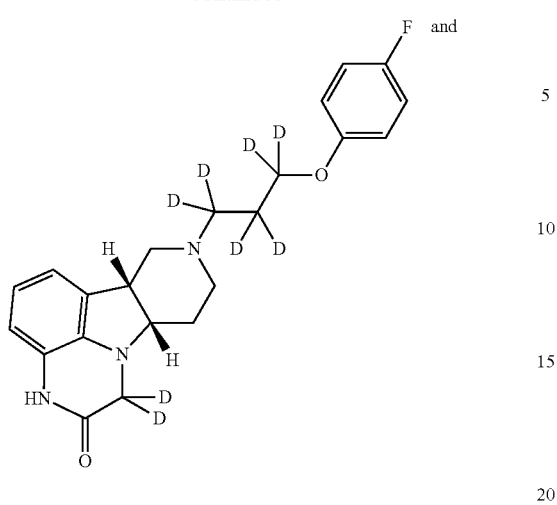
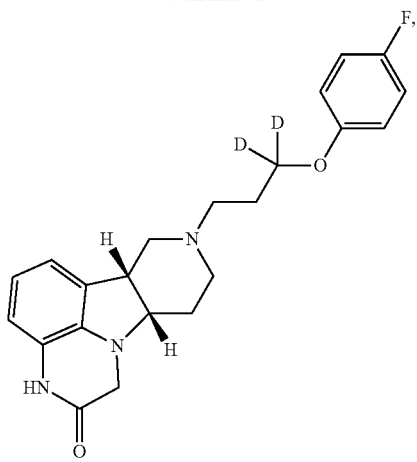
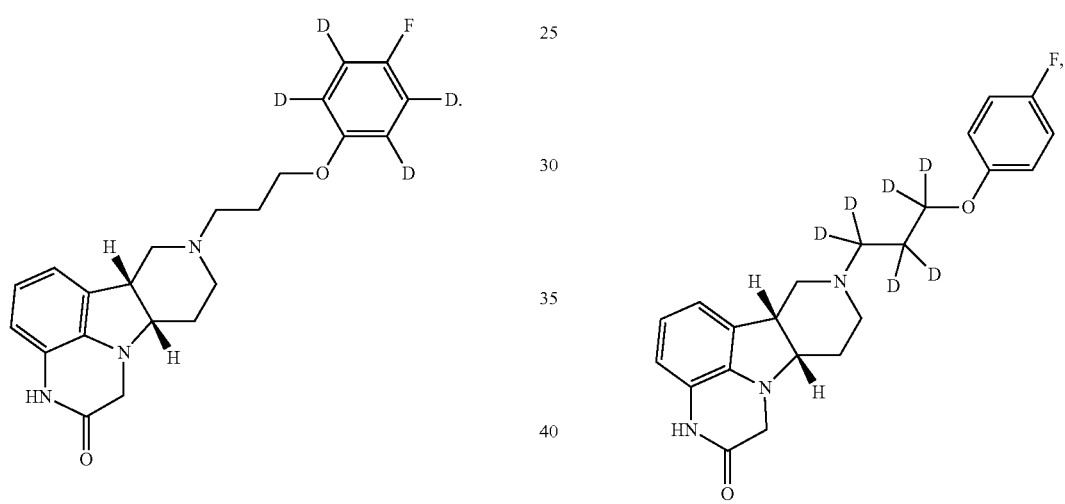
1.24 Compound I or any of 1.1-1.22, wherein the compound is selected from the group consisting of:
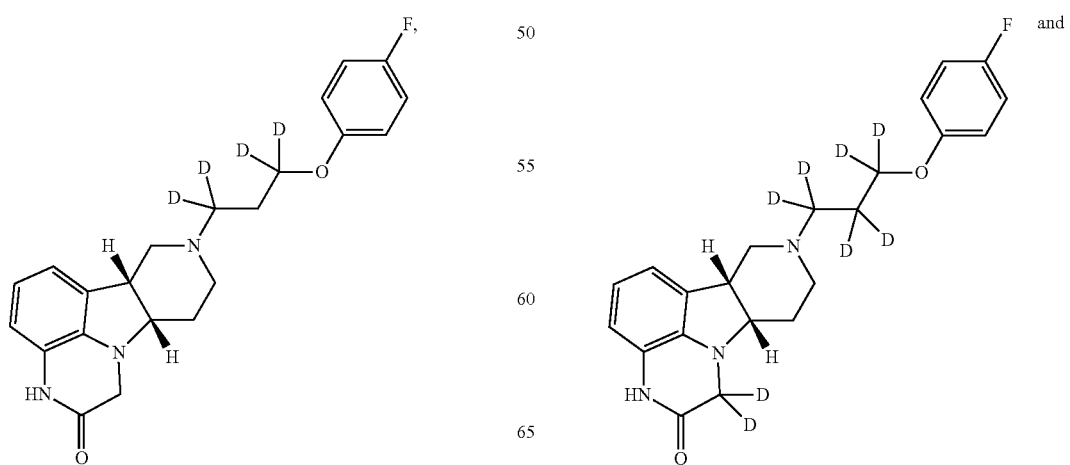

-continued

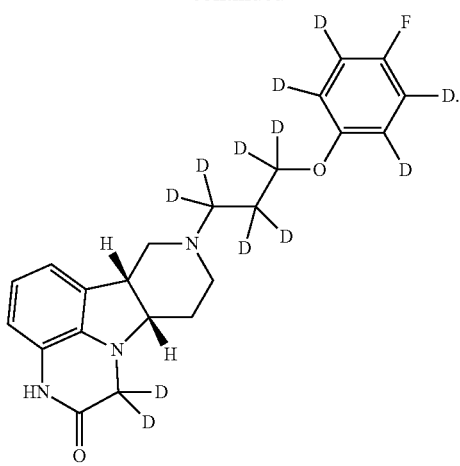

1.25 Compound I or any of 1.1-1.22, wherein the compound is selected from the group consisting of:

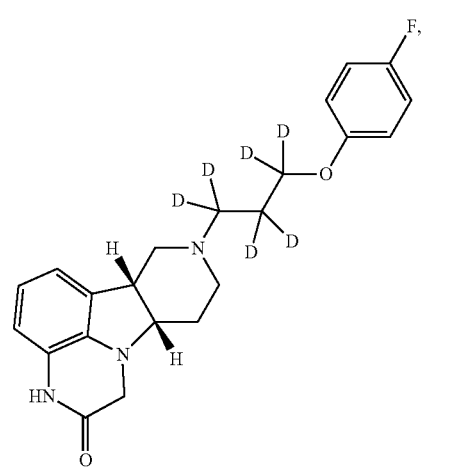

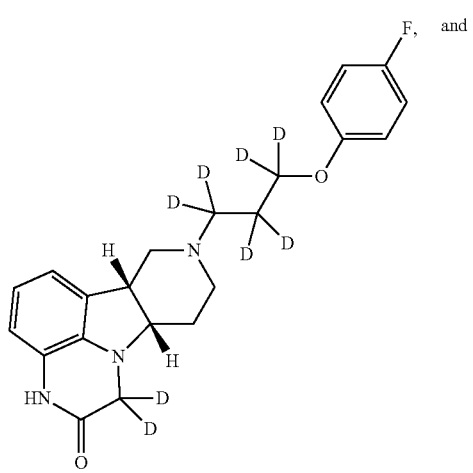

-continued

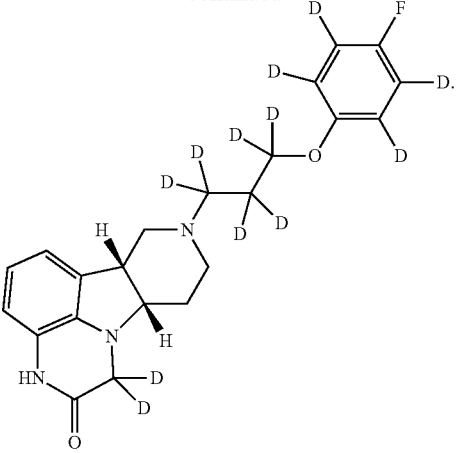

In a second aspect, the present disclosure provides each of the foregoing Compound I or 1.1-1.25, (hereinafter collectively "Compounds of Formulas I et seq." or "compounds of the disclosure") in pharmaceutically acceptable salt form. The present disclosure provides additional exemplary embodiments of the Compounds of Formulas I et seq., including:

2.1 Compounds of Formulas I-II et seq., wherein the salt is an acid addition salt selected from hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;

2.2 Compounds of Formulas I-II et seq., wherein the salt is fumaric acid addition salt;

2.3 Compounds of Formulas I-II et seq., wherein the salt is phosphoric acid addition salt;

2.4 Compounds of Formulas I-II et seq., wherein the salt is a toluenesulfonic acid addition salt;

2.5 Any of 2.1-2.4 wherein the salt is in solid form.

In a third aspect, the present disclosure provides a pharmaceutical composition (Pharmaceutical Composition 3) comprising a compound according to any one of Compound I or 1.1-1.25, e.g., in admixture with a pharmaceutically acceptable diluent or carrier. The present disclosure provides additional exemplary embodiments of Pharmaceutical Composition 1, including:

3.1 Pharmaceutical Composition 3, wherein the Compound of Formula I et seq. is in solid form;

3.2 Pharmaceutical Composition 3 or 3.1, wherein the Compound of Formulas I et seq. is in pharmaceutically acceptable salt form as described in Compounds 2.1-2.5;

3.3 Pharmaceutical Composition 3, or any of 3.1-3.3, wherein the composition is a depot formulation, as described herein (e.g., wherein the composition is formulated as a long-acting injectable, for example, for intramuscular or subcutaneous injection).

3.4 Pharmaceutical Composition 3, or any of 3.1-3.4, wherein the compound of Formula I et seq. is in a polymeric matrix.

In a further embodiment, the Pharmaceutical Compositions of the present disclosure, are for a sustained or delayed release, e.g., depot, formulation. In one embodiment, the depot formulation (Depot Formulation 3.3) is the Pharmaceutical Composition of any of 3.1-3.3, preferably in free or pharmaceutically acceptable salt form, and preferably in admixture with a pharmaceutically acceptable diluent or carrier, e.g., providing sustained or delayed release as an injectable depot.

In a particular embodiment, the Depot Formulation 3.3 comprises a compound according to any one of Compound I or 1.1-1.25, in free base or pharmaceutically acceptable salt form, optionally in crystal form, wherein the compound has been milled to, or the compound crystallized to, microparticle or nanoparticle size, e.g., particles or crystals having a volume-based particle size (e.g., diameter or Dv50) of 0.5 to 100 microns, for example, for example, 5-30 microns, 10-20 microns, 20-100 microns, 20-50 microns or 30-50 microns. Such particles or crystals may be combined with a suitable pharmaceutically acceptable diluent or carrier, for example water, to form a depot formulation for injection. For example, the depot formulation may be formulated for intramuscular or subcutaneous injection with a dosage of drug suitable for 4 to 6 weeks of treatment. In some embodiments, the particles or crystals have a surface area of 0.1 to 5 m$^2$/g, for example, 0.5 to 3.3 m$^2$/g or from 0.8 to 1.2 m$^2$/g.

In another embodiment, the present disclosure provides Pharmaceutical Composition 3.4, which is Pharmaceutical Composition 3 or any of 3.1-3.3, wherein the Compound of Formulas I et seq. is in a polymeric matrix. In one embodiment, the Compound of the present disclosure is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

The (Pharmaceutical) Compositions 3 and 3.1-3.4 are particularly useful for sustained or delayed release, wherein the Compound of the present disclosure is released upon degradation of the polymeric matrix. These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Compositions of the present disclosure, for example the depot composition of the present disclosure, e.g., Pharmaceutical Composition 3.3 or 3.4, is formulated for administration by injection.

In a fourth aspect, the present disclosure provides the Compounds of Formulas I et seq. as hereinbefore described, in an osmotic controlled release oral delivery system (OROS), which is described in WO 2000/35419 (US 2001/0036472) and EP 1 539 115 (U.S. Pub. No. 2009/0202631), the contents of each of which applications are incorporated by reference in their entirety. Therefore in one embodiment of the seventh aspect, the present disclosure provides a pharmaceutical composition or device comprising (a) a gelatin capsule containing a Compound of any of Formulae I et seq. in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Pharmaceutical Composition P.1)

In another embodiment, the invention provides a pharmaceutical composition comprising a gelatin capsule containing a liquid, the Compound of Formulas I et seq. in free or pharmaceutically acceptable salt form or a Pharmaceutical Composition of the Invention, e.g., any of Pharmaceutical Composition 3 or 3.1-3.4, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Pharmaceutical Composition P.2)

In still another embodiment of the fourth aspect, the invention provides a composition comprising a gelatin capsule containing a liquid, the Compound of Formulas I et seq. in free or pharmaceutically acceptable salt form or a Pharmaceutical Composition of the Invention, e.g., any of Pharmaceutical Composition 3 or 3.1-3.4, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Pharmaceutical Composition P.3)

In still another embodiment of the fourth aspect, the invention provides a composition comprising a gelatin capsule containing a liquid, the Compound of Formulas I et seq. in free or pharmaceutically acceptable salt form or a Pharmaceutical Composition of the Invention, e.g., any of Pharmaceutical Composition 3 or 3.1-3.4, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Pharmaceutical Composition P.4). The expandable layer may be formed in one or more discrete sections, such as for example, two sections located on opposing sides or ends of the gelatin capsule.

In a particular embodiment of the fourth aspect, the Compound of the present disclosure in the Osmotic-controlled Release Oral Delivery System (i.e., in Pharmaceutical Composition P.1-P.4) is in a liquid formulation, which formulation may be neat, liquid active agent, liquid active agent in a solution, suspension, emulsion or self-emulsifying composition or the like.

Further information on Osmotic-controlled Release Oral Delivery System composition including characteristics of the gelatin capsule, barrier layer, an expandable layer, a semi-permeable layer; and orifice may be found in WO 2000/35419 (and equivalent US 2001/0036472), the contents of which are incorporated by reference in their entirety.

Other Osmotic-controlled Release Oral Delivery System for the Compound of Formulas I et seq. or the Pharmaceutical Composition of the present disclosure may be found in EP 1 539 115 (U.S. Pub. No. 2009/0202631), the contents of which are incorporated by reference in their entirety. Therefore, in another embodiment of the seventh aspect, the invention provides a composition or device comprising (a) two or more layers, said two or more layers comprising a first layer and a second layer, said first layer comprises the Compound of Formula I et seq., in free or pharmaceutically acceptable salt form, or a Pharmaceutical Composition as herein before described said second layer comprises a polymer; (b) an outer wall surrounding said two or more layers; and (c) an orifice in said outer wall. (Pharmaceutical Composition P.5)

Pharmaceutical Composition P.5 preferably utilizes a semi-permeable membrane surrounding a three-layer-core: in these embodiments, the first layer is referred to as a first drug layer and contains low amounts of drug (e.g., the Compound of Formulas I et seq.) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Pharmaceutical Composition P.6)

Pharmaceutical Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers. (Pharmaceutical Composition P.7)

In a particular embodiment, the invention provides Pharmaceutical Composition P.7 wherein the first drug layer comprising salt and the second drug layer containing no salt. Pharmaceutical Composition P.5-P.7 may optionally comprise a flow-promoting layer between the membrane and the drug layers.

Compositions P.1-P.7 will generally be referred to as Osmotic-controlled Release Oral Delivery System Composition.

In a fifth aspect, the invention provides a method (Method 1) for the treatment or prophylaxis of a central nervous system disorder, comprising administering to a patient in need thereof a Compound of Formulas I et seq. or a Pharmaceutical Composition 3 or 3.1-3.4 or P.1-P.7, for example Method 1 wherein the compound or composition administered is:
1.1 Compound I or any of 1.1-1.25, in free or pharmaceutically acceptable salt form;
1.2 The Compounds of any of formulas 2.1-2.5;
1.3 a Pharmaceutical Composition as described by any of Pharmaceutical Compositions 3 or 3.1-3.4;
1.4 Pharmaceutical Composition P.1-P.7;
1.5 Osmotic-controlled Release Oral Delivery System Composition as hereinbefore described;

In a further embodiment of the fifth aspect, the present disclosure provides Method 1 or any of Methods 1.1-1.5, wherein the method is further as described as follows:
1.6 Method 1 or any of Methods 1.1-1.5, wherein the central nervous system disorder is a disorder selected from a group consisting of obesity, anxiety (including general anxiety, social anxiety, and panic disorders), depression (for example refractory depression and MDD), psychosis (including psychosis associated with dementia, such as hallucinations in advanced Parkinson's disease or paranoid delusions), schizophrenia, sleep disorders (particularly sleep disorders associated with schizophrenia and other psychiatric and neurological diseases), sexual disorders, migraine, pain and conditions associated with pain, including cephalic pain, idiopathic pain, chronic pain (such as moderate to moderately severe chronic pain, for example in patients requiring 24 hour extend treatment for other ailments), neuropathic pain, dental pain, fibromyalgia, chronic fatigue, agoraphobia, social phobias, agitation in dementia (e.g., agitation in Alzheimer's disease), agitation in autism and related autistic disorders, gastrointestinal disorders such as dysfunction of the gastrointestinal tract motility, and dementia, for example dementia of Alzheimer's disease or of Parkinson's disease; mood disorders; drug dependencies, for example, opiate dependency and/or alcohol dependency, and withdrawal from drug or alcohol dependency (e.g., opiate dependency); co-morbidities associated with drug dependencies, such as depression, anxiety and psychosis; binge eating disorder; and obsessive-compulsive disorder (OCD), obsessive-compulsive personality disorder (OCPD) and related disorders;
1.7 Method 1 or any of Methods 1.1-1.6, wherein the central nervous system disorder is a disorder involving serotonin 5-HT$_2$A, dopamine D1 and/or D2 receptor system and/or serotonin reuptake transporter (SERT) pathways as similarly described in US 2011/071080, the contents of which are herein incorporated by reference in their entirety;
1.8 Method 1 or any of Methods 1.1-1.7, wherein the central nervous system disorder is a disorder involving the μ-opioid receptor;
1.9 Method 1 or any of Methods 1.1-1.8, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis and/or drug dependencies, e.g., schizophrenia or Parkinson's disease; (4) sleep disorders associated with psychosis, e.g., schizophrenia or Parkinson's disease; and (5) substance addiction, substance use disorders and/or substance-induced disorders, optionally wherein the patient suffers from residual symptoms of anxiety or anxiety disorder; and optionally wherein the depression is treatment-resistant depression;

1.10 Method 1 or any of Methods 1.1-1.9, wherein the central nervous system disorder is psychosis, e.g., schizophrenia and said patient is a patient suffering from depression;

1.11 Method 1 or any of Methods 1.1-1.10, wherein said patient is unable to tolerate the side effects of conventional antipsychotic drugs, e.g., chlorpromazine, haloperidol, droperidol, fluphenazine, loxapine, mesoridazine molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone and ziprasidone;

1.12 Method 1 or any of Methods 1.1-1.11, wherein said patient is unable to tolerate the side effects of nonnarcotic analgesics and/or opiate and opioid drugs, or wherein the use of opiate drugs are contraindicated in said patient, for example, due to prior substance abuse or a high potential for substance abuse, such as opiate and opioid drugs including, e.g., morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentanyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof.

1.13 Method 1 or any of Methods 1.1-1.12, wherein said patient is unable to tolerate the side effects of conventional antipsychotic drugs, e.g., haloperidol, brexpiprazole, cariprazine, asenapine, lurasidone, aripiprazole, clozapine, olanzapine, quetiapine, risperidone, and ziprasidone;

1.14 Method 1 or any of Methods 1.1-1.13, wherein said disorder is depression and said patient is a patient suffering from psychosis, e.g., schizophrenia, or Parkinson's disease;

1.15 Method 1 or any of Methods 1.1-1.13, wherein said disorder is sleep disorder and said patient is suffering from depression;

1.16 Method 1 or any of Methods 1.1-1.13, wherein said one or more disorders is sleep disorder and said patient is suffering from psychosis, e.g., schizophrenia;

1.17 Method 1 or any of Methods 1.1-1.13, wherein said one or more disorders is sleep disorder and said patient is suffering from Parkinson's disease;

1.18 Method 1 or any of Methods 1.1-1.13, wherein said one or more disorders is sleep disorder and said patient is suffering from depression and psychosis, e.g., schizophrenia, or Parkinson's disease.

1.19 Method 1 or any of 1.1-1.18, wherein said patient is suffering from a drug dependency disorder, optionally in conjunction with any preceding disorders, for example, wherein said patient suffers from opiate dependency, cocaine dependency, amphetamine dependency, and/or alcohol dependency, or from withdrawal from drug or alcohol dependency (e.g. opiate, cocaine, or amphetamine dependency), and optionally wherein the patient suffers from a co-morbidity, such as anxiety, depression or psychosis, or residual symptoms of anxiety or anxiety disorder and/or altered mood (e.g., depression);

1.20 Any of the foregoing methods, wherein the effective amount is 1 mg-1000 mg, for example 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.21 Any of the foregoing methods, wherein the effective amount is 1 mg-100 mg per day, for example 2.5 mg-50 mg per day;

1.22 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

1.23 Any of the foregoing methods wherein the patient suffers from Parkinson's disease.

Substance-use disorders and substance-induced disorders are the two categories of substance-related disorders defined by the Fifth Edition of the DSM (the Diagnostic and Statistical Manual of Mental Disorders. A substance-use disorder is a pattern of symptoms resulting from use of a substance which the individual continues to take, despite experiencing problems as a result. A substance-induced disorder is a disorder induced by use if the substance. Substance-induced disorders include intoxication, withdrawal, substance induced mental disorders, including substance induced psychosis, substance induced bipolar and related disorders, substance induced depressive disorders, substance induced anxiety disorders, substance induced obsessive-compulsive and related disorders, substance induced sleep disorders, substance induced sexual dysfunctions, substance induced delirium and substance induced neurocognitive disorders.

The DSM-V includes criteria for classifying a substance use disorder as mild, moderate or severe. In some embodiments of the methods disclosed herein, the substance use disorder is selected from a mild substance use disorder, a moderate substance use disorder or a severe substance use disorder. In some embodiments, the substance use disorder is a mild substance use disorder. In some embodiments, the substance use disorder is a moderate substance use disorder. In some embodiments, the substance use disorder is a severe substance use disorder.

Anxiety and depression are highly prevalent co-morbid disorders in patients undergoing treatment of substance use or substance abuse. A common treatment for substance abuse disorder is the combination of the partial opioid agonist buprenorphine with the opioid antagonist naloxone, but neither of these drugs has any significant effect on anxiety or depression, thus leading to the common result that a third drug, such as a benzodiazepine-class anxiolytic agent or an SSRI anti-depressant, must also be prescribed. This makes treatment regimens and patient compliance more difficult. In contrast, the Compounds of the present disclosure provide opiate antagonism along with serotonin antagonism and dopamine modulation. This may result in significant enhancement of treatment of patients with substance use or abuse disorder concomitant with anxiety and/or depression.

The compounds of the present disclosure may have anxiolytic properties ameliorating the need for treatment of a patient with an anxiolytic agent where said patients suffers from co-morbid anxiety. Thus, in some embodiments, the present disclosure provides a method according to Method 1, or any of Methods 1.1-1.23, wherein the central nervous system disorder is a substance addiction, substance use disorders and/or substance-induced disorders, or a substance abuse disorder, for example, in a patient suffering from symptoms of anxiety or who is diagnosed with anxiety as a co-morbid disorder, or as a residual disorder, wherein the method does not comprise the further administration of an anxiolytic agent, such as a benzodiazepine. Benzodiazepines are GABA-modulating compounds, including those discussed with reference to Method 3.1 and 3.2 below.

In another embodiment of the fifth aspect, the present disclosure provides Method 1 or any of Methods 1.1-1.7, wherein the method is further as described as follows:

1.24 Method 1 or any of Methods 1.1-1.23, wherein the central nervous system disorder is a disorder selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD), impulse control disorder, and related disorders, and combination thereof.

1.25 Method 1 or any one Method 1.1-1.23, wherein the central nervous system disorder is selected from obsessive-compulsive disorder (OCD), obsessive-compulsive personality disorder (OCPD), social anxiety disorder, panic disorder, agoraphobia, compulsive gambling disorder, compulsive eating disorder, body dysmorphic disorder and impulse control disorder.

1.26 Method 1 or any one of Method 1.1-1.23, wherein the central nervous system disorder is obsessive-compulsive disorder (OCD) or obsessive-compulsive personality disorder (OCPD).

1.27 Any foregoing method, wherein said patient is not responsive to or cannot tolerate the side effects from, treatment with selective serotonin reuptake inhibitors (SSRIs), such as citalopram, escitalopram, fluoxetine, fluvoxamine, paroxetine, and sertraline.

1.28 Any foregoing method, wherein said patient is not responsive to or cannot tolerate the side effects from, treatment with serotonin-norepinephrine reuptake inhibitors (SNRIs), such as venlafaxine, sibutramine, duloxetine, atomoxetine, desvenlafaxine, milnacipran, and levomilnacipran.

1.29 Any foregoing method, wherein said patient is not response to or cannot tolerate the side effects from, treatment with antipsychotic agents, such as clomipramine, risperidone, quetiapine and olanzapine.

1.30 Any of the foregoing methods, wherein the effective amount is 1 mg-1000 mg, preferably 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.31 Any of the foregoing methods, wherein the effective amount is 1 mg-100 mg per day, preferably 2.5 mg-50 mg per day.

In still another embodiment, the present disclosure provides any of the Methods 1 or 1.1-1.31 as hereinbefore described wherein the disorder is schizophrenia or sleep disorder. In some embodiments, said schizophrenia is associated with depression.

In still another embodiment, the present disclosure provides any of Methods 1.1-1.31, wherein the Pharmaceutical Composition 3 or 3.1-3.4, or Pharmaceutical Composition P.1-P.7, is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In still another embodiment, the invention provides any Method 1 or 1.1-1.31 as hereinbefore described, wherein the Depot Composition of the present disclosure is administered for controlled- and/or sustained-release of the Compounds of the Invention over a period of time.

In a sixth aspect, the invention provides a method (Method 2) for the prophylaxis or treatment of one or more sleep disorders comprising administering to a patient in need thereof a Compound of Formulas I et seq. or a Pharmaceutical Composition 3 or 3.1-3.4 or P.1-P.7, (Method 2) for example Method 2 wherein the compound or composition administered is:

2.1 Compound I or 1.1-1.25, in free or pharmaceutically acceptable salt form;
2.2 Compound 5.1-5.5;
2.3 a Pharmaceutical Composition as described by any of Pharmaceutical Composition 3 or 3.1-3.4;
2.4 Pharmaceutical Composition P.1-P.7;
2.5 Osmotic-controlled Release Oral Delivery System Composition as hereinbefore described;

In a further embodiment of the sixth aspect, the invention provides Method 2, or 2.1-2.5, wherein the sleep disorder includes sleep maintenance insomnia, frequent awakenings, and waking up feeling unrefreshed; for example:

2.6 Any of the foregoing methods, wherein the sleep disorder is sleep maintenance insomnia;
2.7 Any of the foregoing methods, wherein the effective amount is 1 mg-5 mg, preferably 2.5-5 mg, per day;
2.8 Any of the foregoing methods, wherein the effective amount is 2.5 mg or 5 mg, per day;
2.9 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;
2.10 Any of the foregoing methods wherein the patient suffers from Parkinson's disease.

In a further embodiment of the sixth aspect, the invention provides Method 2, or any of 2.1-2.10, wherein the sleep disorder includes sleep maintenance insomnia, frequent awakenings, and waking up feeling unrefreshed.

The Compounds of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the present disclosure may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the present disclosure in combination with one or more second therapeutic agents in free or salt form, wherein the dosages of (i) the second therapeutic agent(s) or (ii) both Compound of the present disclosure and the second therapeutic agents, are lower than if the agents/compounds are administered as a monotherapy. In a particular embodiment, the Compounds of the present disclosure are useful to treat dyskinesia in a patient receiving dopaminergic medications, e.g., selected from levodopa and levodopa adjuncts (carbidopa, COMT inhibitors, MAO-B inhibitors), dopamine agonists, and anti-cholinergics, e.g., such as are used in the treatment of Parkinson's disease.

Therefore, in a seventh aspect, the present disclosure provides Method I, or any of Methods 1.1-1.31, or Method 2 or any of 2.1-2.10, further comprising the administration of one or more therapeutic agents to the patient, wherein the one or more therapeutic agents is selected from compounds that modulate GABA activity (e.g., enhances the activity and facilitates GABA transmission), a GABA-B agonist, a 5-HT receptor modulator (e.g., a $5\text{-HT}_{1A}$ agonist, a $5\text{-HT}_{2A}$ antagonist, a $5\text{-HT}_{2A}$ inverse agonist, etc.), a melatonin receptor agonist, an ion channel modulator (e.g., blocker), a serotonin-2 receptor antagonist/reuptake inhibitor (a compound having both $5\text{-HT}_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and opiate agonist and/or partial opiate agonist (such as a mu-, kappa- or delta-opiate receptor agonist or partial agonist), nociceptin agonist, and an antipsychotic agent, e.g., an atypical antipsychotic agent, in free or pharmaceutically acceptable salt form (Method I-A and II-A respectively; collectively, "Method 3").

In further embodiments of the seventh aspect, the present disclosure provides Method I, or any of Methods 1.1-1.31, or Method 2 or any of 2.1-2.10, further comprising the administration to the patient of one or more therapeutic agents selected from the foregoing and further selected from agonists or partial agonists of the mu-opiate, kappa-opiate, delta-opiate, and/or nociceptin/orphanin receptors. In further embodiments of the tenth aspect, the present disclosure also provides Method I, or any of Methods 1.1-31, or Method 2 or any of 2.1-2.10, further comprising one or more therapeutic agents selected from a serotonin HT6 receptor antagonist, and an mGluR-2, -3 or -5 receptor agonist or antagonist (including both positive and negative modulators and partial agonists).

In a further embodiment of the seventh aspect, the invention provides Method 3 (i.e., Method I-A or II-A), wherein the method further comprises the administration of one or more therapeutic agents to the patient, as follows:

3.1 Method I-A or II-A, wherein the therapeutic agent(s) is compounds that modulate GABA activity (e.g., enhances the activity and facilitates GABA transmission);

3.2 Method I-A or II-A or 3.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals) and estazolam;

3.3 Method I-A or II-A, wherein the therapeutic agent is an additional 5HT2a receptor antagonist;

3.4 Method I-A or II-A or 3.3, wherein said additional 5HT2a receptor antagonist is selected from one or more of pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), and AVE8488 (Sanofi-Aventis, France);

3.5 Method I-A or II-A, wherein the therapeutic agent is a melatonin receptor agonist;

3.6 Method I-A or II-A or 3.5, wherein the melatonin receptor agonist is selected from a group consisting of one or more of melatonin, ramelteon (ROZEREM®, Takeda Pharmaceuticals, Japan), VEC-162 (Vanda Pharmaceuticals, Rockville, MD), PD-6735 (Phase II Discovery) and agomelatine;

3.7 Method I-A or II-A, wherein the therapeutic agent is an ion channel blocker;

3.8 Method I-A or II-A or 3.7, wherein said ion channel blocker is one or more of lamotrigine, gabapentin and pregabalin.

3.9 Method I-A or II-A, wherein the therapeutic agent is an orexin receptor antagonist;

3.10 Method I-A or II-A or 3.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

3.11 Method I-A or II-A, wherein the therapeutic agent is the serotonin-2 receptor antagonist/reuptake inhibitor (SARI);

3.12 Method I-A or II-A or 3.11, wherein the serotonin-2 receptor antagonist/reuptake inhibitor (SARI) is selected from a group consisting of one or more Org 50081 (Organon-Netherlands), ritanserin, nefazodone, serzone and trazodone;

3.13 Method I-A or II-A, wherein the therapeutic agent is the 5HTIa agonist;

3.14 Method I-A or II-A or 3.13, wherein the 5HTIa agonist is selected from a group consisting of one or more of repinotan, sarizotan, eptapirone, buspirone and MN-305 (MediciNova, San Diego, CA);

3.15 Method I-A or II-A, wherein the therapeutic agent is the neurokinin-1 drug;

3.16 Method I-A or II-A or 3.15, wherein the neurokinin-1 drug is Casopitant (GlaxoSmithKline);

3.17 Method I-A or II-A, wherein the therapeutic agent is an antipsychotic agent;

3.18 Method I-A or II-A or 3.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.19 Method I-A or II-A, wherein the therapeutic agent is an anti-depressant;

3.20 Method I-A or II-A or 3.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine;

3.21 Method I-A or II-A, 3.17 or 3.18, wherein the antipsychotic agent is an atypical antipsychotic agent;

3.22 Method I-A or II-A, or any of 3.17-3.21, wherein the atypical antipsychotic agent is selected from a group consisting of brexpiprazole, cariprazine, asenapine, lurasidone, clozapine, aripiprazole, olanzapine, quetiapine, risperidone, ziprasidone, and paliperidone;

3.23 Method I-A or II-A, wherein the therapeutic agent is selected from any of methods 3.1-3.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam, pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.24 Method I-A or II-A wherein the therapeutic agent is an H3 agonist;

3.25 Method I-A or II-A, wherein the therapeutic agent is an H3 antagonist;

3.26 Method I-A or II-A, wherein the therapeutic agent is a noradrenergic agonist or antagonist;

3.27 Method I-A or II-A, wherein the therapeutic agent is a galanin agonist;

3.28 Method I-A or II-A, wherein the therapeutic agent is a CRH antagonist;

3.29 Method I-A or II-A, wherein the therapeutic agent is a human growth hormone;

3.30 Method I-A or II-A, wherein the therapeutic agent is a growth hormone agonist;

3.31 Method I-A or II-A, wherein the therapeutic agent is estrogen;

3.32 Method I-A or II-A, wherein the therapeutic agent is an estrogen agonist;

3.33 Method I-A or II-A, wherein the therapeutic agent is a neurokinin-1 drug;

3.34 Method I-A or II-A, wherein a therapeutic agent is combined with compounds of Formula (I) and the therapeutic agent is an anti-Parkinson agent such as L-dopa, co-careldopa, duodopa, stalevo, Symmetrel, benztropine, biperiden, bromocriptine, entacapone, pergolide, pramipexole, procyclidine, ropinirole, selegiline and tolcapone;

3.35 Method I-A or II-A, wherein the therapeutic agent is an opiate agonist or partial opiate agonist, for example, a mu-agonist or partial agonist, or a kappa-agonist or partial agonist, including mixed agonist/antagonists (e.g., an agent with partial mu-agonist activity and kappa-antagonist activity);

3.36 Method 3.35, wherein the therapeutic agent is buprenorphine, optionally, wherein said method does not include co-treatment with an anxiolytic agent, e.g., a GABA compound or benzodiazepine;

3.37 Method I-A or II-A, wherein compounds of Formula (I) may be used to treat sleep disorders, depression, psychosis, or any combinations thereof, in patients suffering from the listed diseases and/or Parkinson's disease;

3.38 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

3.39 Any of the foregoing methods wherein the disorder is sleep disorder;

3.40 Any of the foregoing methods, wherein the disorder is sleep disorder associated with psychosis, e.g., schizophrenia or Parkinson's disease; in free or pharmaceutically acceptable salt form.

In an eighth aspect of the invention, the combination of a Compound of the present disclosure and one or more second therapeutic agents as described in Methods I-A, II-A or any of Methods 3 or 3.1-3.40 may be administered to the patient as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, 3 or 3.1-3.40 comprises administering to a patient in need thereof, a Compound of the Invention in combination with an atypical antipsychotic agent, e.g., a compound selected from brexpiprazole, cariprazine, asenapine, lurasidone, clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, 3 or 3.1-3.40 comprises administering to the patient in need thereof, a Compound of the Invention in combination with an anti-depressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compound of the Invention.

In still another embodiment, Methods I-A, II-A, 3 or 3.1-3.40 comprises administering to the patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam or any combinations thereof, in free or pharmaceutically acceptable salt form. In other embodiments, the methods disclosed herein do not further comprise administration of an GABA compound, a benzodiazepine or any other anxiolytic agent.

In another preferred embodiment, Methods I-A, II-A, 3 or 3.1-3.40 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, 3 or 3.1-3.40 comprises administering to a patient in need thereof, a Compound of the Invention in combination (including as part of a daily dosage regimen) with an a typical stimulant, e.g., a modafinil, adrafinil, or armodafinil A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In some of the foregoing embodiments, each of the Compounds of Formulas I et seq.; Pharmaceutical Compositions 3 and 3.1-3.4; Compositions P.1-P.7; Methods 1 and 1.1-1.31; and Methods 2 and 2.1-2.10 and 3 and 3.1-3.40; the compound of the present disclosure is substantially free of compound of Formula A and/or Formula B.

In a ninth aspect, the invention provides use of a compound as described in the following:

9.1 Compound I or 1.1-1.25, in free or pharmaceutically acceptable salt form;

9.2 Compound 5 or 5.1-5.5;

9.3 Pharmaceutical Composition 3 or 3.1-3.4;

9.4 Pharmaceutical Composition P.1-P.7;

9.5 Osmotic-controlled Release Oral Delivery System Composition as hereinbefore described;

(in the manufacture of a medicament) for the treatment or prophylaxis of one or more disorders as disclosed hereinbefore, e.g., in any of Method 1 or 1.1-1.31, any of Method 2 and 2.1-2.10, and Method 3 or 3.3-3.40, or any methods described in the tenth aspect of the invention.

In the tenth aspect, the invention provides a pharmaceutical composition as hereinbefore described, e.g.:

10.1 Pharmaceutical Composition 3 or 3.1-3.4;

10.2 Pharmaceutical Composition P.1-P.7;

10.3 Osmotic-controlled Release Oral Delivery System Composition as hereinbefore described, for use in the treatment or prophylaxis of one or more disorders as disclosed hereinbefore, e.g., in any of Methods 1 and 1.1-1.31, Methods 2 and 2.1-2.10, Methods I-A, II-A, 3 or 3.1-3.40 or any methods described in the eighth or ninth aspects of the invention.

DETAILED DESCRIPTION OF THE INVENTION

If not otherwise specified or clear from context, the following terms as used herein have the following meetings:

Without being bound by theory, the current invention provides compounds which specifically limit, slow, alter and/or prevent the metabolism which has been found to occur in animals treated with the compounds such as the Compound A and Compound B:

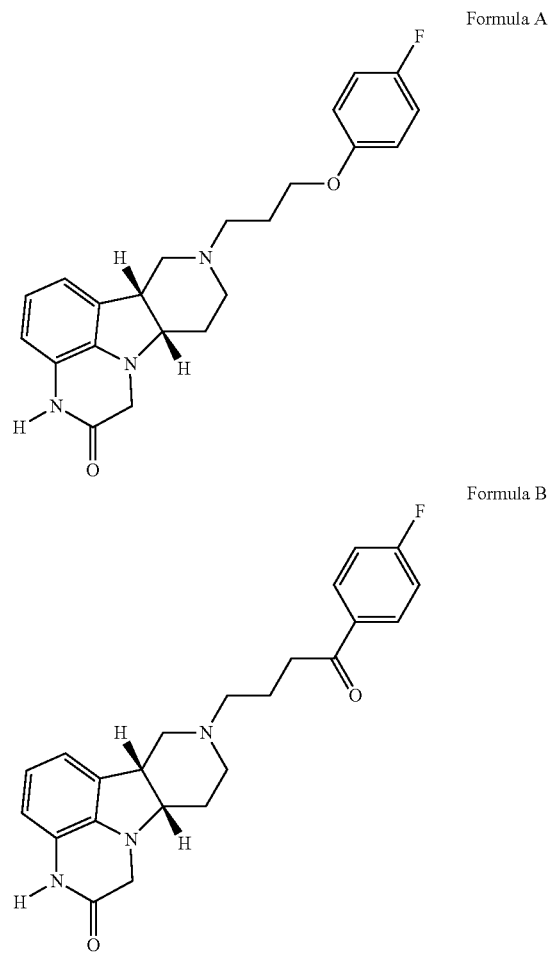

Formula A

Formula B

Due to the very similar chemical and physical properties of deuterium ($^2$H) atoms compared to normal hydrogen atoms ($^1$H), e.g., atomic charge, atomic volume, polarity, valency, etc., drug compounds in which deuterium is substituted for hydrogen are believed to generally have similar biological activity to the non-deuterated analog, but potentially with improved pharmacokinetic properties. It is particularly important that while deuterium atoms have almost double the atomic mass of protium atoms, their space volume and charge distribution are similar, these latter factors being critical in binding to biological molecules. Improved pharmacokinetic properties results from the significantly higher bond strength of a C-D bond compared to an H-D bond, and consequently, the higher energy barrier to D/H abstraction during an enzymatic (metabolic) reaction (the kinetic isotope effect). The extent to which such a substitution will result in an improvement of pharmacokinetic properties without a too severe loss in pharmacologic activity is variable. Thus, in some circumstances, the resulting deuterated compound only a moderate increase in pharmacokinetic stability, while in other circumstances, the resulting deuterated compound may have significantly improved stability. Moreover, it may be difficult to predict with certainty the effects of simultaneous deuterium substitutions. These may or may not result in additive (synergistic) improvement in metabolic stability.

Although many deuterated pharmaceutical compounds have been proposed and explored to date, only one deuterated pharmaceutical compound has been approved by the U.S. Food and Drug Administration, deutetrabenazine (Teva Pharmaceuticals, April 2017), a deuterated version of the Huntington's disease drug tetrabenazine, which has a therapeutically useful longer half-life than its non-deuterated counterpart.

The current disclosure provides compounds containing deuterium atoms at specific selected positions of the structure of compounds of Formula A and/or Formula B. These particular deuterations are expected to have in impact on metabolic degradation and clearance of said compounds because of their relationship to enzymatic pathways determined by the inventors to likely affect these compounds. These novel compounds are therefore expected to antagonize 5-HT$_{2A}$ receptors, inhibit the serotonin re-uptake transporter, modulate dopaminergic protein phosphorylation, and modulate mu-opiate receptor activity, in a like manner as to their natural hydrogen analogs, yet with unexpectedly improved metabolic stability and pharmacokinetic properties.

"Alkyl" as used herein is a saturated or unsaturated hydrocarbon moiety, e.g., one to twenty-one carbon atoms in length, unless indicated otherwise; any such alkyl may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example in some embodiments wherein $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The term "D" or "deuterium" refers to the $^2$H-isotope of the atom hydrogen. The natural abundance of the two stable isotopes of hydrogen are about 99.98% protium ($^1$H), and 0.02% deuterium ($^2$H). Thus, on average, any hydrogen atom in a molecule synthesized using common reagents will have approximately 0.02% deuterium at every hydrogen atom position. Thus, the skilled artisan would understand that when reference is made to a chemical structure having a C-D bond or a "D" atom, as described herein, this means that said position of the molecule is enriched to have more than the natural 0.02% abundance of deuterium. Thus, a label "D" in a molecule indicates, e.g., at least 0.1% deuterium, or at least 1% deuterium, or at least 10% deuterium. Preferably, any compound according to the present disclosure has greater than 50% incorporation of deuterium at each specified "D" atom position of the compound's structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan.

Unless otherwise indicated, the Compounds of the present disclosure, e.g., Compound I or 1.1-1.25 may exist in free or salt, e.g., as acid addition salts, form. An acid-addition salt of a compound of the invention which is sufficiently basic, for example, an acid-addition salt with, for example, an inorganic or organic acid, for example hydrochloric, hydrobromic, sulphuric, phosphoric, acid acetic, trifluoroacetic, citric, maleic acid, toluene sulfonic, propionic, succinic, glycolic, stearic, lactic, malic, tartaric, citric, ascorbic, pamoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition, a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the Compounds of the Invention is a toluenesulfonic acid addition salt.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included within the scope of the compounds of the present disclosure.

The Compounds of the present disclosure may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Thus, in addition to the deuteration specifically provided for by the scope of the compounds of Formula I, the present disclosure further envisions compounds according to Formula I wherein one or more carbon atoms, nitrogen atoms or oxygen atoms are replaced by a stable or unstable isotopic variant (e.g., $^{11}C$, $^{13}C$ $^{15}N$, $^{18}O$, $^{18}F$), and further wherein one or more hydrogen atoms are replaced by tritium ($^{3}H$). These compounds are useful, e.g., for structural determinations (e.g., by nuclear magnetic resonance or mass spectral analysis) and for the purpose of radioimaging studies to elucidate metabolic and excretory pathways and to measure clearance of potential drug candidates.

Compounds of the present disclosure may be included as a depot formulation, e.g., by dispersing, dissolving or encapsulating the Compounds of the Invention in a polymeric matrix as described in any of Composition 3 and 3.1-3.4, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d, 1-lactide-co-glycolide) have a central glucose moiety having rays of linear polylactide chains.

The depot compositions of the invention (e.g., Compositions 6 and 6.1-6.10, in a polymer matrix) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the present disclosure incorporated in the microparticles usually ranges from about 1 wt % to about 90 wt. %, preferably 30 to 50 wt. %, more preferably 35 to 40 wt. %. By weight % is meant parts of the Compounds of the present disclosure per total weight of microparticle.

The pharmaceutical depot compositions may comprise a pharmaceutically-acceptable diluent or carrier, such as a water miscible diluent or carrier.

Details of Osmotic-controlled Release Oral Delivery System composition may be found in EP 1 539 115 (U.S. Pub. No. 2009/0202631) and WO 2000/35419 (US 2001/0036472), the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, are preferably administered parenterally, e.g., by injection.

In general, satisfactory results for Method 1 and 1.1-1.31, Method 2 and 2.1-2.10, and Method 3 and 3.1-3.40, or use of the Compounds of the present disclosure as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; (4) sleep disorders associated with psychosis, e.g., schizophrenia, or Parkinson's disease; and (5) substance addiction, substance use disorders and/or substance-induced disorders, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration.

Satisfactory results for Method 2 or 2.1-2.10 or use of the Compounds of the present disclosure as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

Satisfactory results for Method I-A or Method II-A, or any of 3.1-3.40 are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 3.1-3.40 are indicated to be obtained at less than 5 mg, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the present disclosure may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069 (each equivalent to US 2011/112105).

Pharmaceutical compositions comprising Compounds of the present disclosure may be prepared using conventional diluents or excipients (an example include, but is not limited to sesame oil) and techniques known in the galenic art. Thus oral dosage forms may include tablets, capsules, solutions, suspensions and the like.

Methods of Making the Compounds of the Invention:

Methods for the synthesis of compounds of Formula A and B, including the intermediates therefor, have been disclosed in International Application PCT/US2017/15178, published as WO 2017/132408, and in US patent publication US 2017/319580.

The essential core of other Compounds of the present disclosure came be made by analogous procedures disclosed in the above-reference publications and known to those skilled in the art. The particular deuterated compounds of the present disclosure may generally be prepared by analogous means by substituting commercially available deuterated reagents for non-deuterated reagents, when such deuterated reagents are available.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Salts of the Compounds of the present disclosure may be prepared as similarly described in U.S. Pat. Nos. 6,548,493; 7,238,690; 6,552,017; 6,713,471; 7,183,282; U.S. RE39680; U.S. RE39679; and WO 2009/114181 (US 2011/112105), the contents of each of which are incorporated by reference in their entirety.

Diastereomers of prepared compounds can be separated by, for example, HPLC using CHIRALPAK® AY-H, 5μ, 30×250 mm at room temperature and eluted with 10% ethanol/90% hexane/0.1% dimethylethylamine Peaks can be detected at 230 nm to produce 98-99.9% ee of the diastereomer.

Example 1: Synthesis of (6bR,10aS)-1,1-d$_2$-8-(3-(4-fluorophenoxy)propyl)-6b,7,8,9,10,10a-hexahydro-1H-pyrido[3',4':4,5]pyrrolo[1,2,3-de]quinoxalin-2(3H)-one

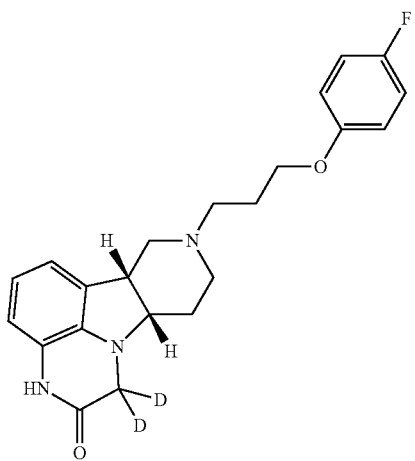 [SMILES: [2H]C1([2H])C(=O)Nc2cccc3c2N1[C@H]1CCN(CCCOc2ccc(F)cc2)C[C@@H]31]

Step 1: To a degassed mixture of (4aS,9bR)-ethyl 6-bromo-3,4,4a,5-tetrahydro-1H-pyrido[4,3-b]indole-2(9bH)-carboxylate (1.60 g, 8.0 mmol), 2-chloro-2,2-di-deuterioacetamide (2.5 g, 26 mmol), and KI (2.68 g, 16 mmol) in dioxane (30 mL), diisopropylethylamine (3.0 mL, 16 mmol) is added at room temperature. The reaction mixture is then heated to 104° C. under vigorous stirring for 5 days. Solvents are removed under vacuum and the residue is suspended in dichloromethane (50 mL) and extracted with water (20 mL). The organic phase is separated, dried over anhydrous K$_2$CO$_3$ and concentrated to a residue. The product is purified by silica gel column chromatography using a gradient of 0-100% ethyl acetate in hexanes to obtain (4aS,9bR)-ethyl 5-(2-amino-1,1-d$_2$-2-oxoethyl)-6-bromo-3,4,4a,5-tetrahydro-1H-pyrido[4,3-b]indole-2(9bH)-carboxylate as a brown oil (1.26 g, yield 41%). MS (ESI) m/z 384.1 [M+1]. The synthesis of the starting material is disclosed in US 2010/113781. The reaction scheme is shown below:

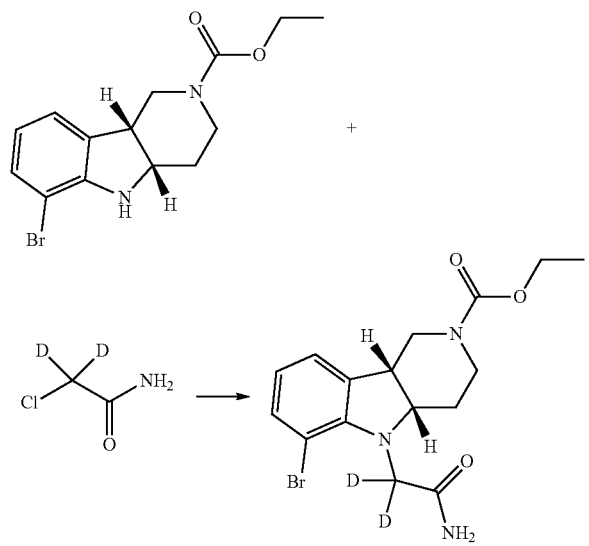

Step 2: To a degassed mixture of the product from Step 1 (1.26 g, 3.3 mmol), K$_2$CO$_3$ (1.0 g, 6.0 mmol), CuI (132 mg, 0.69 mmol) in dioxane (6 mL), and N,N,N',N'-tetramethyl-ethylenediamine (0.3 mL, 12.0 mmol) is added at room temperature. The reaction mixture is heated to 99° C. and stirred at this temperature for 20 h. After cooling to room temperature, the mixture is directly loaded on a silica gel column. The product is purified by silica gel column chromatography using 100% ethyl acetate to obtain (6bR,10aS)-ethyl 1,1-d$_2$-2-oxo-2,3,6b,7,10,10a-hexahydro-1H-pyrido[3',4':4,5]pyrrolo[1,2,3-de]quinoxaline-8(9H)-carboxylate as a light red solid (680 mg, yield 68%). MS (ESI) m/z 318.2 [M+1]+. The reaction scheme is shown below:

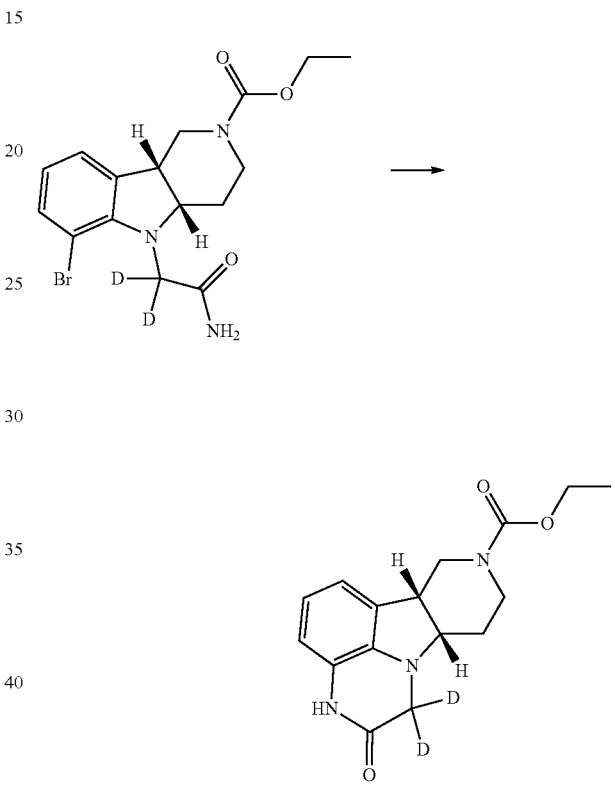

Step 3: The product from Step 2 (680 mg, 2.24 mmol) is suspended in HBr solution (33% in acetic acid, 10 ml) at room temperature. The mixture is heated to 70° C., and stirred at 70° C., for additional 2 h. LC-MS confirms the completion of reaction. The reaction mixture is cooled to room temperature and further cooled with ice. Ethyl acetate (60 mL) is added to precipitate the product salt. The solid is filtered and dried under vacuum. The HBr salt of product is suspended in methanol (20 mL) and is cooled with dry ice and 2-propanol. Ammonia (7N in methanol) is added slowly until the pH is at or above 14. The solvents are then removed under vacuum to yield crude (6bR,10aS)-1,1-d$_2$-6b,7,8,9,10,10α-hexahydro-1H-pyrido[3',4':4,5]pyrrolo[1,2,3-de]quinoxalin-2(3H)-one as a brown solid (227 mg, yield 44%). The crude product is used directly in the next step without any further purification. MS (ESI) m/z 232.2 [M+1]$^+$. The reaction scheme is shown below:

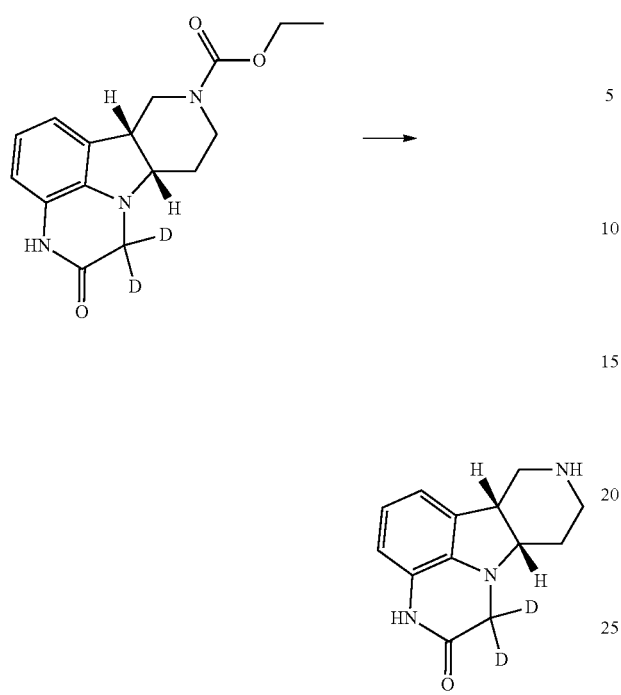

Step 4: A mixture of the crude product from Step 3 (227 mg, 0.98 mmol), 1-(3-chloroproxy)-4-fluorobenzene (320 μL, 2.0 mmol) and KI (330 mg, 2.0 mmol) in DMF (4 mL) is bubbled with argon for 3 minutes and DIPEA (350 μL, 2 mmol) is added. The resulting mixture is heated to 76° C. and stirred at this temperature for 2 h. After cooling to room temperature, the solvent is removed and the residue is purified by silica gel column chromatography using a gradient of 0-100% mixed solvents [ethyl acetate/methanol/7N NH$_3$ (10:1:0.1 v/v)] in ethyl acetate to obtain the title product as a brown solid (110 mg, yield 28%). $^1$H NMR (500 MHz, DMSO-d$_6$) δ 10.34 (s, 1H), 7.14-7.06 (m, 2H), 6.97-6.89 (m, 2H), 6.77 (d, J=6.7 Hz, 1H), 6.64 (td, J=7.5, 1.1 Hz, 1H), 6.58 (d, J=7.8 Hz, 1H), 3.97 (t, J=6.4 Hz, 2H), 3.30-3.17 (m, 2H), 2.92-2.81 (m, 1H), 2.70-2.58 (m, 1H), 2.47-2.28 (m, 2H), 2.10 (t, J=11.6 Hz, 1H), 1.99-1.90 (m, 1H), 1.90-1.75 (m, 3H), 1.74-1.61 (m, 1H). MS (ESI) m/z 384.2 [M+1]$^+$. The reaction scheme is shown below:

Example 2: Synthesis of (6bR,10aS)-8-(1,1,2,2,3,3-d$_6$-3-(4-fluorophenoxy)propyl)-6b,7,8,9,10,10a-hexahydro-1H-pyrido[3',4': 4,5]pyrrolo[1,2,3-de]quinoxalin-2(3H)-one Step 1: To degassed CH$_3$CN (5 mL), p-fluorophenol (442 mg, 4.0 mmol), 1,3-dibromopropane-d$_6$ (1.02 g, 4.9 mmol) and K$_2$CO$_3$ (608 mg, 4.4 mmol) are added under stirring. The resulting mixture is heated to 80° C. and stirred at 80° C. overnight. After cooling to room temperature, the solvent is removed and the residue is suspended in dichloromethane (50 mL) and extracted with water (20 mL). The aqueous phase is separated and extracted further with dichloromethane (10 mL). The combined organic phase is dried over anhydrous Na$_2$CO$_3$ and concentrated to yield crude the product, 1-(3-bromo-1,1,2,2,3,3-d$_6$-propoxy)-4-fluorobenzene as a colorless oil. 0.98 g crude product is obtained, which is used directly in the next step without further purification. The reaction scheme is shown below:

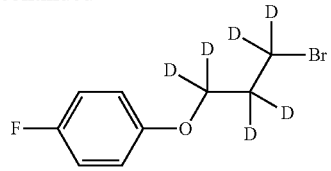

Step 2: A mixture of (6bR,10aS)-6b,7,8,9,10,10a-hexahydro-1H-pyrido[3',4':4,5]pyrrolo[1,2,3-de]quinoxalin-2(3H)-one HBr salt (900 mg, 2.9 mmol), 1-(3-bromo-1,1,2,2,3,3-d6-propoxy)-4-fluorobenzene (500 mg, 2.1 mmol) and potassium iodide (500 mg, 3.6 mmol) in DMF (5 mL) is bubbled with argon for 3 min, and di-isopropyl ethylamine (550 μL, 3.16 mmol) is added. The resulting mixture is heated to 78° C. and stirred at this temperature for 2 h. After cooling to room temperature, the solvent is removed and the residue is suspended in dichloromethane (50 mL) and extracted with water (20 mL). The aqueous phase is separated and further extracted with dichloromethane (10 mL). The combined organic phase is dried over anhydrous $Na_2CO_3$ and concentrated. The final product is purified by silica gel column chromatography using a gradient of 0-80% mixed solvents [ethyl acetate/methanol/7N $NH_3$ (10:1:0.1 v/v/v)] in ethyl acetate to obtain the title product as a light brown solid (400 mg, yield 49%). $^1$H NMR (500 MHz, Chloroform-d) δ 7.73 (s, 1H), 7.00-6.90 (m, 2H), 6.89-6.77 (m, 3H), 6.77-6.69 (m, 1H), 6.61 (d, J=7.7 Hz, 1H), 3.95 (d, J=14.5 Hz, 1H), 3.59-3.19 (m, 3H), 3.10-2.59 (m, 2H), 2.28 (s, 1H), 2.01 (t, J=16.0 Hz, 3H). MS (ESI) m/z 388.2 [M+1]+. The reaction scheme is shown below:

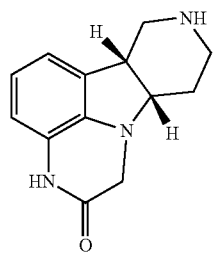

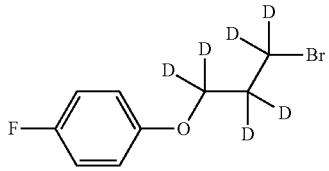

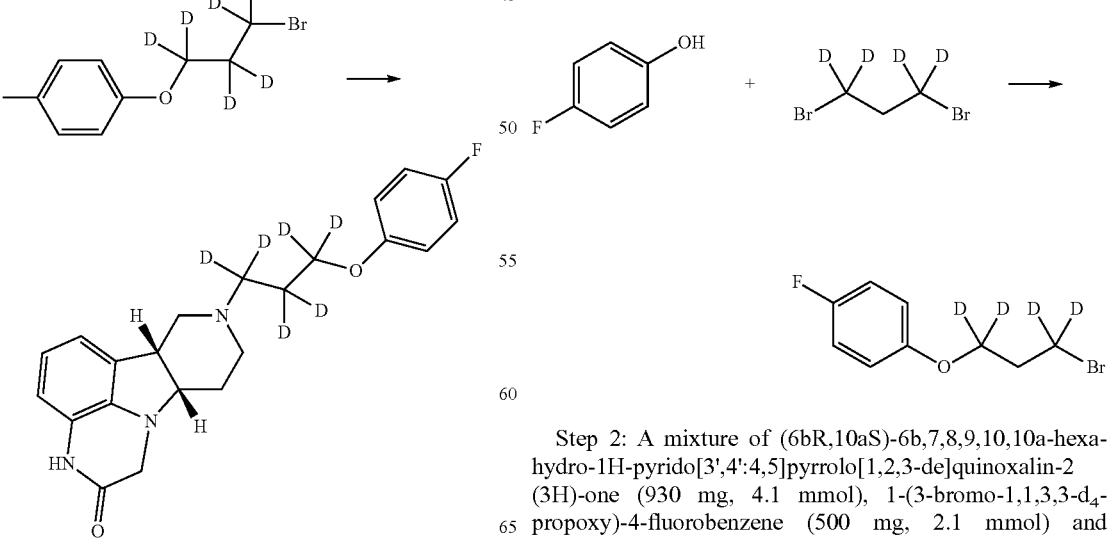

Example 3: Synthesis of (6bR,10aS)-8-(1,1,3,3-d4-3-(4-fluorophenoxy)propyl)-6b,7,8,9,10,10a-hexahydro-1H-pyrido[3',4':4,5]pyrrolo[1,2,3-de]quinoxalin-2(3H)-one

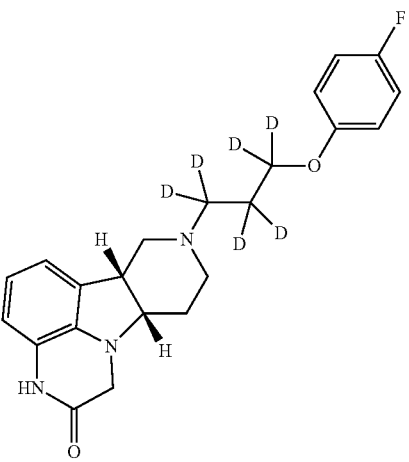 [SMILES: [2H]C([2H])(Oc1ccc(F)cc1)C([2H])([2H])C([2H])([2H])N1CC[C@H]2[C@@H](C1)c1cccc3c1N2CC(=O)N3]

Step 1: To a degassed $CH_3CN$ (5 mL), p-fluorophenol (546 mg, 4.9 mmol), 1,3-dibromo-1,1,3,3-d4-propane (1.1 g, 5.4 mmol) and $K_2CO_3$ (730 mg, 5.4 mmol) are added under stirring. The resulting mixture is heated to 80° C. and stirred at 80° C. for 21 h. After cooling to room temperature, the solvent is removed and the residue is suspended in dichloromethane (50 mL) and extracted with water (20 mL). The aqueous phase is separated and further extracted with dichloromethane (10 mL). The combined organic phase is dried over anhydrous $MgSO_4$ and concentrated to yield the crude product, 1-(3-bromo-1,1,3,3-d4-propoxy)-4-fluorobenzene as a light-yellow oil (0.82 g). It is used directly in the next step without further purification. The reaction scheme is shown below:

Step 2: A mixture of (6bR,10aS)-6b,7,8,9,10,10a-hexahydro-1H-pyrido[3',4':4,5]pyrrolo[1,2,3-de]quinoxalin-2(3H)-one (930 mg, 4.1 mmol), 1-(3-bromo-1,1,3,3-d4-propoxy)-4-fluorobenzene (500 mg, 2.1 mmol) and potassium iodide (560 mg, 3.4 mmol) in DMF (5 mL) is bubbled with argon for 3 min, and diisopropyl ethylamine (550 μL, 3.2 mmol) is added. The resulting mixture is heated to 78° C. and stirred at this temperature for 2 h. After cooling to room temperature, the solvent is removed and the residue is suspended in dichloromethane (50 mL) and extracted with water (20 mL). The aqueous phase is separated and extracted further with dichloromethane (10 mL×2). The combined organic phase is dried over anhydrous MgSO₄ and concentrated. The final product is purified by silica gel column chromatography using a gradient of 0-80% mixed solvents [ethyl acetate/methanol/7N NH₃ (10:1:0.1 v/v)] in ethyl acetate and the product is further purified with basic alumina column chromatography using a gradient of 0-100% mixed solvents [ethyl acetate/methanol (20:1 v/v)] in ethyl acetate. The title product is obtained as a white solid (248 mg, yield 31%). ¹H NMR (500 MHz, Chloroform-d) δ 7.80 (s, 1H), 7.01-6.88 (m, 2H), 6.87-6.77 (m, 3H), 6.73 (t, J=7.6 Hz, 1H), 6.59 (dd, J=7.8, 1.0 Hz, 1H), 3.96 (d, J=14.6 Hz, 1H), 3.39 (d, J=14.5 Hz, 1H), 3.37-3.24 (m, 2H), 2.92 (d, J=9.9 Hz, 1H), 2.74 (s, 1H), 2.25 (d, J=14.3 Hz, 1H), 1.98 (dd, J=37.6, 12.2 Hz, 5H). MS (ESI) m/z 386.2 [M+1]⁺. The reaction scheme is shown below:

Example 4: Synthesis of 6bR,10aS)-8-(3-(4-fluoro-phenoxy)propyl)-6b,7,8,9,10,10a-hexahydro-1H-pyrido[3',4':4,5]pyrrolo[1,2,3-de]quinoxalin-2(3H)-one (the compound of Formula A) and 4-((6bR, 10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one (the compound of Formula B)

US 2017/319580, discloses the synthesis of the compounds of Formula A and B as Examples 3 and 1, respectively, therein:

Formula A

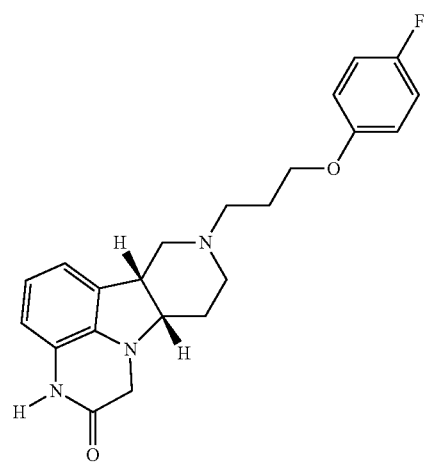

Formula B

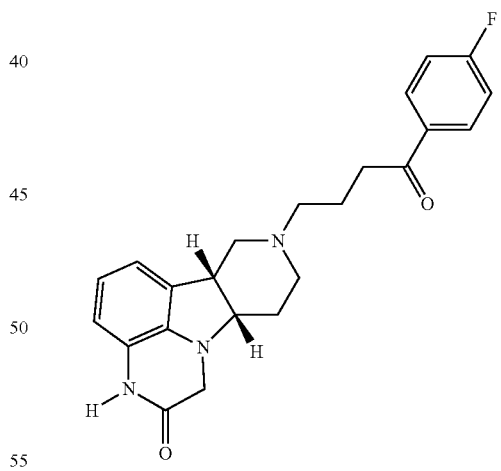

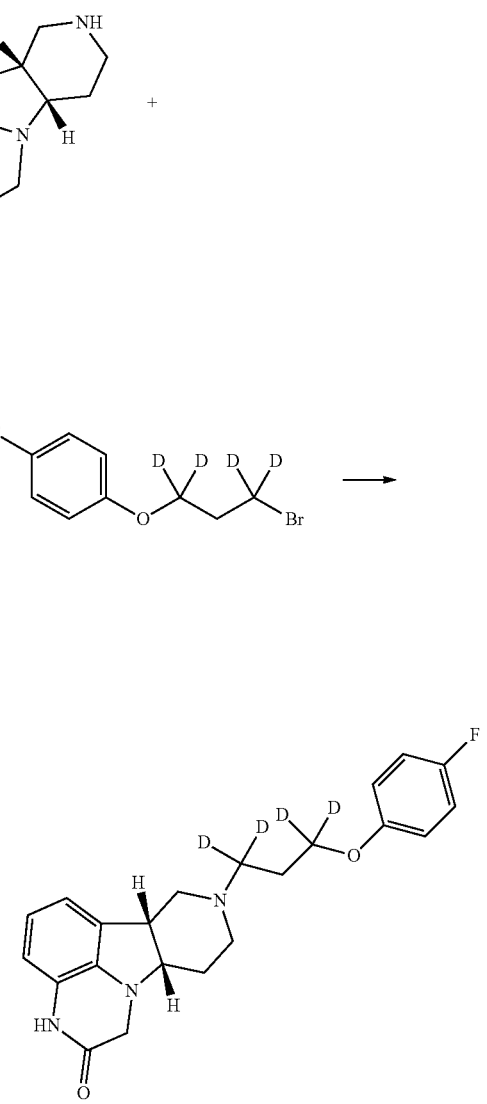

The compound of Formula A and the compound of Formula B are both prepared from (6bR, 10aS)-2-oxo-2,3,6b,9,10,10a-hexahydro-1H,7H-pyrido[3',4':4,5]pyrrolo[1,2,3-de]quinoxaline-8-carboxylic acid ethyl ester. This carbamate ester is first deprotected using HBr/acetic acid solution. The resulting amine is then reacted with the appropriate alkylating agent (1-(3-chloroproxy)-4-fluorobenzene for the compound of Formula A; 4-chloro-4'-fluorobutyrophenone for the compound of Formula B) to yield the desired product.

Example 5: Experimental properties of (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one (the compound of Formula A) and 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one (the compound of Formula B)

US 2017/319580 discloses several experimental data evaluating the pharmacological properties of the compounds of Formula A and B, in Examples 1-10 therein. In addition, U.S. Provisional Application No. 62/639,244 (and WO 2019/023062) discloses additional properties for these compounds. These disclosures are summarized below.

Cellular and Nuclear Receptor Functional Assays are performed on the compound of Formula B to determine the agonist and antagonist effects of the compound on the human mu-opiate receptor. It is found that the compound has an antagonist effect with an $IC_{50}$ of $1.3 \times 10^{-6}$ M, and a KB of $1.4 \times 10^{-7}$ M.

A Receptor Binding Profile study is conducted on the Compound of Formula B, with the results expressed as a percent of control specific binding, and $IC_{50}$ values and Hill coefficients (nH) are determined by non-linear regression analysis. The following receptor affinity results are obtained:

| Receptor | Ki (nM) or maximum inhibition | |
|---|---|---|
| | Formula B | Formula A |
| $5-HT_{2A}$ | 11 | 8.3 |
| D2 | 47% inhibition at 240 nM | 160 |
| D1 | 22 | 50 |
| SERT | 44% inhibition at 240 nM | 590 |
| Mu opiate receptor | 22 | 11 |

The compounds of Formula A and B are also compared against buprenorphine (a mu-opiate partial agonist), naloxone (a mu-opiate antagonist), and DAMGO (a mu-opiate full agonist) in a both agonist and antagonist functional receptor activity assays using CHO-K1 cells expressing human mu-opiate receptor (μ1 subtype). The results are shown in Table below. The results demonstrate that the compound of Formula A is a weak antagonist of the Mu receptor, showing much higher $IC_{50}$ compared to naloxone, and that it is a moderately high affinity, but partial agonist,

| Compound | Antagonist IC50 (nM) | Agonist EC50 (nM) | KB (nM) |
|---|---|---|---|
| Naloxone | 5.80 | — | 0.65 |
| DAMGO | — | 1.56 | — |
| Buprenorphine | — | 0.95 | — |
| Formula A | 641 | 64.5 | 71.4 |
| Formula B | — | 140 | — |

The compounds of Formula A and B are also studied in a mouse DOI-Induced Head Twitch Model. R-(−)-2,5-dimethoxy-4-iodoamphetamine (DOI) is an agonist of the serotonin $5-HT_2$ receptor family. When administered to mice, it produces a behavioral profile associated with frequent head twitches. The frequency of these head twitches during a predetermined period of time can be taken as an estimate of $5-HT_2$ receptor agonism or antagonism in the brain. On oral dosing of mice 30 minutes after subcutaneous injection of DOI, the following results are obtained, which demonstrates that both compounds are effective at blocking DOI-induced head twitch:

| Compound | $EC_{50}$ (mg/kg, p.o.) |
|---|---|
| Formula B | 0.23 |
| Formula A | 0.44 |

The compounds of Formula A and B are also studied in a Mouse Tail Flick Assay, a measure of analgesia indicated by the pain reflex threshold of restrained mice. Male CD-1 mice are positioned with their tails under a focused beam of high-intensity infrared heat source, resulting in heating of the tail. The amount of time (latency) between turning on heating instrument and the flicking of the mouse's tail out of path of the heat source is recorded. Administration of morphine results in analgesia, and this produces a delay in the mouse's reaction to the heat (increased latency). Prior administration of a morphine (MOR) antagonist, i.e., naloxone (NAL), reverses the effect and results in normal latency time. This test is used as a functional assay to gauge antagonism of mu-opiate receptors. Group 1 mice are a negative control, receiving vehicle both 60 minute and 30 minutes prior to the test. Group 2 and 3 mice are positive controls, receiving vehicle followed by morphine or naloxone followed by morphine, respectively, prior to the test. Group 4, 5 and 6 mice are the study subjects receiving the Compound of Formula A or B at one of three doses 60 minutes before the test and morphine 30 minutes before the test. The results of the study are shown below as mean tail flick latency measured in seconds:

| | Group 1 Veh/Veh | Group 2 Veh/Mor | Group 3 Nal/Mor | Group 4 Cmpd/Mor (0.1 mg/kg) | Group 5 Cmpd/Mor (0.3 mg/kg) | Group 6 Cmpd/Mor (1 mg/kg) |
|---|---|---|---|---|---|---|
| Form. B | 1.028 | 9.361 | 2.496 | 8.870 | 6.907 | 6.240 |
| Form. A | 0.887 | 8.261 | 3.013 | 6.947 | 5.853 | 6.537 | showing only about 22% agonist activity relative to DAMGO (as compared to about 79% activity for buprenorphine relative to DAMGO). The compound of Formula B is also shown to have moderately strong partial agonist activity.

A second similar mouse tail flick study is performed to examine the effects on mice treated with naloxone prior to treatment with the compound of Formula A at three different doses. The results are shown in the table below as mean latency in seconds:

|  | Vehicle | Morphine | Form. A at 1 mg/kg | Form. A at 3 mg/kg | Form. A at 10 mg/kg |
|---|---|---|---|---|---|
| Saline pre-treatment | 0.9 | 9.8 | 4.1 | 7.4 | 9.8 |
| Naloxone pre-treatment | 0.8 | 1.5 | 1.3 | 1.7 | 2.1 |

The first study demonstrates that the compounds of Formula A and B both exert a dose-dependent blockade of morphine-induced mu-opiate receptor activity. The second study demonstrates that the compound of Formula A, at higher doses, exerts a dose-dependent mu-opiate agonist activity. Thus, these compounds are partial agonists and partial antagonists of the mu-opiate receptor.

The compounds of Formula A and B are also evaluated in a mouse CNS Phosphoprotein Profile assay. The extent of protein phosphorylation for selected key central nervous system proteins is measured in mice nucleus accumbens. Examined proteins include ERK1, ERK2, GluI, NR2B and TH (tyrosine hydroxylase), and results are compared to the antipsychotic agents risperidone and haloperidol. The results show that neither the compound of Formula A nor the compound of Formula B has a significant effect on TH phosphorylation or NR2B phosphorylation, and that they have marginal effects on GluR1 and ERK2 phosphorylation. In contrast, haloperidol produces a 400-500% increase in TH phosphorylation, suggesting that the compounds of Formula A and B do not disrupt dopamine metabolism.

The compound of Formula A is also studied in the mouse marble-burying model for OCD. The marble burying test is used to measure repetitive and anxiety-related behavior in rodents. It is based on the observation that rats and mice will bury either harmful or harmless objects in their bedding, and it has been used as an animal model to measure the effect of pharmacological interventions in treatment of repetitive behavior disorders, such as OCD. MPEP (2-methyl-6-(phenylethynyl)pyridine), a selective mGluR5 glutamate receptor antagonist, is used as a positive control. Mice are administered a desired agent and placed in a cage with marbles and bedding, and after 30 minutes the number of marbles buried by the mouse is measured. The results are shown in the table below, and demonstrate that a dose-dependent reduction in OCD symptoms for the compound of Formula A.

| Group | Marbles Buried |
|---|---|
| (1) Vehicle | 13.2 |
| (2) 0.3 mg/kg Form. A | 9.3 |
| (3) 1.5 mg/kg Form. A | 4.7 |
| (4) MPEP | 0.2 |

The compound of Formula A is further assessed during repeated (28 day) daily subcutaneous administration to male Sprague-Dawley rats to monitor drug effects on dosing and to determine if pharmacological tolerance occurs. Morphine is used as a positive control to ensure validity of the model and as a reference comparator from a similar pharmacological class. The results show that repeated administration of the Compound of Example 3, at both 0.3 and 3 mg/kg four times, does not produce tolerance during subcutaneous dosing for 28 days. Furthermore, on withdrawal, a similar but decreasing profile of behavioral and physical signs is observed at the highest dose, which is not considered to be of clinical significance. Thus, overall the Compound of Example 3 was found not to produce a syndrome of physical dependence upon cessation of dosing. In contrast, repeated morphine administration is shown to produce clear signs of tolerance and dependence in this study, with changes in body weight, food and water intake, rectal temperature and clinical signs consistent with the development of tolerance and withdrawal induced dependence.

The Compound of Formula A is also evaluated in an oxycodone-dependent withdrawal study in mice. Oxycodone is administered to mice in increasing doses over 8 days to induce physical dependent. On the night day, the mice are administered the compound of Formula A at one of two doses, followed either by an injection of vehicle or of naloxone. The mice are then monitored for signs and symptoms of opiate withdrawal. The results demonstrate that the compound of Formula A dose-dependently reduces the signs and symptoms of opiate withdrawal after the sudden cessation of opiate administration in opiate-dependent rats The Compound of Formula A is also evaluated in an in the mouse formalin paw test, an inflammatory pain model. Subcutaneous injection of 2.5% formalin solution into the hind paw of mice results in a biphasic response: an acute pain response and a delayed inflammatory response. 30 minutes prior to formalin challenge, the same paw is pre-treated with a subcutaneous injection of vehicle, morphine or the compound of Formula A in one of three doses. The results demonstrate that the compound of Formula A dose-dependently attenuates both the early phase acute pain response and the late phase delayed inflammatory response to extent comparable to the morphine positive control.

Example 6: (6bR,10aS)-8-(3-(2,3,5,6-tetradeuterio-4-fluorophenoxy)propyl)-6b,7,8,9,10,10a-hexahydro-1H-pyrido[3',4':4,5]pyrrolo[1,2,3-de]quinoxalin-2(3H)-one

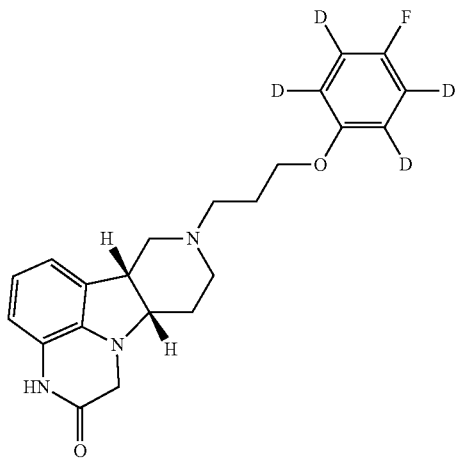 [SMILES: [2H]c1c([2H])c(OCCCN2CC[C@H]3[C@@H](C2)c2cccc4c2N3CC(=O)N4)c([2H])c([2H])c1F]

To a degassed DMF (2 mL), p-fluorophenol-d5 (250 mg, 2.13 mmol) is added under stirring. The resulting solution is cooled with ice for 5 min. NaH (≈70 mg, 95%) is added to the above solution in one portion, and the mixture is stirred for 10 min at room temperature. A solution of 1,3-dibromopropane (650 µL) in DMF (2 mL) is added dropwise. The mixture is stirred at room temperature for 3.5 hours, and then it is stirred at 75° C. overnight. The reaction mixture is cooled and then filtered. The filtrate is concentrated, and the obtained crude product is purified by silica gel column chromatography using a gradient of 0-10% ethyl acetate in hexanes to obtain 1-(3-bromopropoxy)-4-fluoro-2,3,5,6-d$_4$-benzene as a colorless oil (60 mg, yield 12%).

A mixture of (6bR,10aS)-6b,7,8,9,10,10a-hexahydro-1H-pyrido[3',4':4,5]pyrrolo[1,2,3-de]quinoxalin-2(3H)-one (230 mg, 1.0 mmol), 1-(3-bromopropoxy)-4-fluoro-2,3,5,6-d$_4$-benzene (60 mg, 0.25 mmol) and KI (49 mg, 0.35 mmol) in DMF (4 mL) is bubbled with argon for 3 min and then DIPEA (50 µL, 0.28 mmol) is added. The resulting mixture is heated to 76° C. and stirred at this temperature for 2 h. After cooling to room temperature, the solvent is removed and the residue is purified by silica gel column chromatography using a gradient of 0-100% mixed solvents [ethyl acetate/methanol/7N NH$_3$ (10:1:0.1 v/v)] in ethyl acetate to obtain the title product as a white solid (35 mg, yield 9.1%). $^1$H NMR (500 MHz, DMSO-d$_6$) δ 10.34 (s, 1H), 6.77 (dd, J=7.2, 1.0 Hz, 1H), 6.63 (t, J=7.5 Hz, 1H), 6.58 (dd, J=7.8, 1.1 Hz, 1H), 3.97 (t, J=6.4 Hz, 2H), 3.80 (d, J=14.6 Hz, 1H), 3.30-3.14 (m, 3H), 2.92-2.80 (m, 1H), 2.70-2.59 (m, 1H), 2.46-2.30 (m, 2H), 2.16-2.04 (m, 1H), 2.01-1.90 (m, 1H), 1.90-1.74 (m, 3H), 1.68 (t, J=11.0 Hz, 1H). MS (ESI) m/z 386.2 [M+1]+.

Example 7: Synthesis of (6bR,10aS)-8-(3,3-dideuterio-3-(4-fluorophenoxy)propyl)-6b,7,8,9,10,10a-hexahydro-1H-pyrido[3',4':4,5]pyrrolo[1,2,3-de]quinoxalin-2(3H)-one

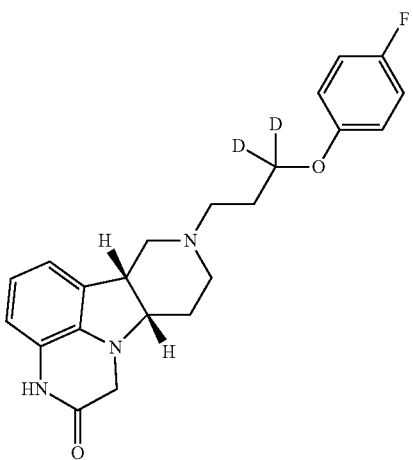 [SMILES: [2H]C([2H])(CCN1CC[C@H]2[C@@H](C1)c1cccc3c1N2CC(=O)N3)Oc1ccc(F)cc1]

Step 1: To a mixture of LiAlD$_4$ (850 mg, 20.2 mmol) in THF (25 mL) at 0° C. under vigorous stirring is added 3-(benzyloxy) propanoic acid (3.2 g, 17.7 mmol) in batches. The mixture temperature is kept under 5° C. during addition process. The mixture is then stirred at room temperature overnight and cooled to 0° C. Water (0.85 mL) and NaOH (15%, 0.85 mL) are slowly added to quench the reaction. The solvents are removed and the residue is diluted with dichloromethane (100 mL) and dried over MgSO$_4$. MgSO$_4$ is filtered and the filtrate is evaporated to dryness. The product 3-(benzyloxy)-1,1-dideuteriopropan-1-ol is obtained as a pale solid (2.86 g, yield 96%). This product is used directly in the next step without further purification.

Step 2: Crude 3-(benzyloxy)-1,1-dideuteriopropan-1-ol (2.4 g, 14.3 mmol) from Step 1 is dissolved in THF (30 mL) and p-fluorophenol (1.6 g, 14.3 mmol) is added, followed by PPh$_3$ (3.75 g, 14.3 mmol). To this mixture under stirring, diethyl azodicarboxylate (2.3 mL, 14.6 mmol) is slowly dropped. The mixture temperature is kept within 40-50° C. during the addition process. After stirring at room temperature overnight, the reaction mixture is evaporated to dryness. The residue is purified by silica gel column chromatography using a gradient of 0-15% ethyl acetate in hexane as eluent. The product 1-(3-(benzyloxy)-1,1-dideuteriopropoxy)-4-fluorobenzene is obtained as a pale solid (1.89 g, yield 50%).

Step 3: Palladium on activated charcoal (10%, 0.5 g) is added to a solution of 1-(3-(benzyloxy)-1,1-dideuteriopropoxy)-4-fluorobenzene (1.89 g, 7.2 mmol) in methanol (45 mL) at room temperature. The mixture is degassed and backfilled with hydrogen three times and then stirred at room temperature for 12 h under hydrogen atmosphere. After the reaction being finished, the solid is filtered and the filtrate is evaporated to dryness. The residue is dissolved in dichloromethane (40 mL) and N, N-diisopropylethylamine (1.7 mL, 11 mmol) is added. The reaction solution is cooled to 0° C. and mesyl chloride (0.65 mL, 7.9 mmol) is dropped within one minute. The reaction mixture is then gradually warmed up to room temperature under stirring. After stirring at room temperature for 0.5 h, the reaction is quenched with water (20 mL). The organic phase is separated and dried over MgSO$_4$ and filtered. The filtrate is evaporated to dryness to yield crude product 3,3-dideuterio-3-(4-fluorophenoxy)propyl methanesulfonate (1.93 g, yield 100%). This product is used directly for next reaction without further purification. MS (ESI) m/z 251.2 [M+H]+.

Step 4: A mixture of crude (6bR,10aS)-6b,7,8,9,10,10a-hexahydro-1H-pyrido[3',4':4,5]pyrrolo[1,2,3-de]quinoxalin-2(3H)-one (520 mg, 2.3 mmol) and 3,3-dideuterio-3-(4-fluorophenoxy)propyl methanesulfonate (530 mg, 2.1 mmol) in DMF (4 mL) is bubbled with argon for 3 min, and DIPEA (500 µL, 2.6 mmol) is added. The resulting mixture is heated to 78° C. and stirred at this temperature for 2 h. The mixture is then cooled to room temperature, and DMF is removed. The residue is treated with dichloromethane (30 mL) and extracted with water (10 mL). The organic phase is separated and dried over K$_2$CO$_3$ and filtered. The filtrate is concentrated and purified by semi-preparative HPLC using a gradient of 0-20% acetonitrile in water with 0.1% formic acid as eluent. The title product is obtained as a green solid (121 mg, yield 14%). $^1$H NMR (500 MHz, DMSO-d$_6$) δ 10.35 (s, 1H), 7.09 (dd, J=9.8, 7.9 Hz, 2H), 6.97-6.88 (m, 2H), 6.77 (dd, J=7.2, 1.1 Hz, 1H), 6.63 (t, J=7.6 Hz, 1H), 6.57 (dd, J=7.8, 1.2 Hz, 1H), 3.80 (d, J=14.6 Hz, 1H), 3.33-3.27 (m, 1H), 3.27-3.16 (m, 2H), 2.86 (dd, J=11.5, 6.3 Hz, 1H), 2.69-2.57 (m, 1H), 2.45-2.26 (m, 2H), 2.09 (td, J=11.8, 2.5 Hz, 1H), 1.94 (dt, J=14.2, 2.5 Hz, 1H), 1.89-1.73 (m, 3H), 1.67 (t, J=11.0 Hz, 1H). MS (ESI) m/z 396.2 [M+1]±.

Example 8: Synthesis of (6bR,10aS)-1,1-dideuterio-8-(1,1,2,2,3,3-hexadeuterio-3-(2,3,5,6-tetradeuterio-4-fluorophenoxy)propyl)-6b,7,8,9,10,10a-hexahydro-1H-pyrido[3',4':4,5]pyrrolo[1,2,3-de]quinoxalin-2(3H)-one

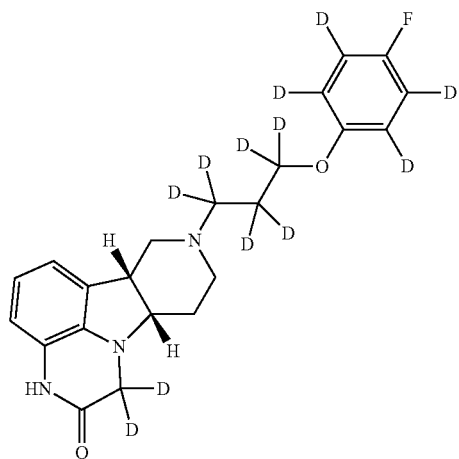 [SMILES: [2H]c1c([2H])c(OC([2H])([2H])C([2H])([2H])C([2H])([2H])N2CC[C@H]3[C@@H](C2)c2cccc4c2N3C([2H])([2H])C(=O)N4)c([2H])c([2H])c1F]

To a degassed suspension of 4-fluorophenol-d$_5$ (500 mg, 4.3 mmol), and K$_2$CO$_3$ (690 mg, 4.9 mmol) in acetonitrile (5 mL) is added 1,3-dibromo-1,1,2,2,3,3-hexadeuteriopropane (1.0 g, 4.8 mmol) under stirring. The resulting mixture is heated to 80° C. and stirred at this temperature overnight. After cooling to room temperature, the reaction mixture is concentrated, and the residue is suspended in water (20 mL) and extracted with dichloromethane (2×30 mL). The combined dichloromethane phase is dried over Na$_2$CO$_3$ and filtered. The filtrate is concentrated to yield a crude product 1-(3-bromo-1,1,2,2,3,3-hexadeuteriopropoxy)-2,3,5,6-tetradeuterio-4-fluorobenzene as a colorless oil (1.0 g, yield: 95%). This product is used directly for next step without further purification.

A mixture of (6bR,10aS)-1,1-dideuterio-6b,7,8,9,10,10a-hexahydro-1H-pyrido[3',4':4,5]-pyrrolo[1,2,3-de]quinoxalin-2(3H)-one HBr salt (500 mg, 2.2 mmol), 1-(3-bromo-1,1,2,2,3,3-hexadeuteriopropoxy)-2,3,5,6-tetradeuterio-4-fluorobenzene (500 mg, 2.0 mmol), and KI (380 mg, 2.3 mmol) in DMF (5 mL) is bubbled with argon for 3 min, and di-isopropyl ethylamine (400 μL, 4.8 mmol) is added. The resulting mixture is heated to 78° C. and stirred at this temperature for 2 h. After cooling to room temperature, the solvent is removed and the residue is suspended in dichloromethane (50 mL), and extract the mixture with water (20 mL). The aqueous phase is separated and extracted with dichloromethane (10 mL). The combined organic phase is dried over Na$_2$CO$_3$ and filtered. The filtrate is concentrated and purified by silica gel column chromatography using a gradient of 0-100% mixed solvents [ethyl acetate/methanol/7N NH$_3$ (10:1:0.1 v/v)] in ethyl acetate to give a brown solid (230 mg). This brown product is further purified by semi-preparative HPLC using a gradient of 0-20% acetonitrile in water with 0.1% formic acid as eluent. The title product is obtained as a white solid (80 mg, 9% yield). $^1$H NMR (500 MHz, DMSO-d$_6$) δ 10.35 (s, 1H), 6.78 (d, J=7.2 Hz, 1H), 6.64 (td, J=7.5, 1.2 Hz, 1H), 6.58 (dd, J=7.7, 1.1 Hz, 1H), 3.30-3.25 (m, 1H), 3.22 (dt, J=10.7, 6.4 Hz, 1H), 2.86 (ddt, J=11.3, 6.2, 1.9 Hz, 1H), 2.64 (ddt, J=11.4, 4.7, 2.4 Hz, 1H), 2.17-2.02 (m, 1H), 1.95 (dt, J=14.3, 2.6 Hz, 1H), 1.80 (ddt, J=14.2, 12.1, 4.7 Hz, 1H), 1.68 (tdd, J=10.7, 6.0, 4.4 Hz, 1H). MS (ESI) m/z 394.2 [M+1]$^+$.

Example 9: Synthesis of (6bR,10aS)-1,1-dideuterio-8-(1,1,2,2,3,3-hexadeuterio-3-(4-fluorophenoxy)propyl)-6b,7,8,9,10,10a-hexahydro-1H-pyrido[3',4':4,5]pyrrolo[1,2,3-de]quinoxalin-2(3H)-one

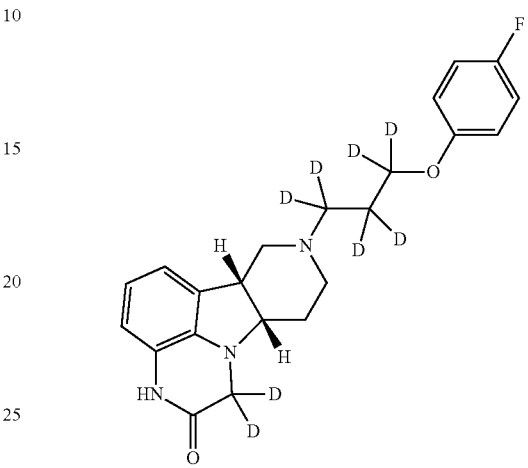

Step 1: To a degassed suspension of 4-fluorophenol (442 mg, 4.0 mmol), and K$_2$CO$_3$ (608 mg, 4.4 mmol) in acetonitrile (5 mL) is added 1,3-dibromo-1,1,2,2,3,3-hexadeuteriopropane (1.0 g, 4.8 mmol) under stirring. The resulting mixture is heated to 80° C. and stirred at this temperature overnight. After cooling to room temperature, the reaction mixture is concentrated, and the residue is suspended in water (20 mL) and extracted with dichloromethane (2×30 mL). The combined dichloromethane phase is dried over Na$_2$CO$_3$ and filtered. The filtrate is concentrated to yield a crude product 1-(3-bromo-1,1,2,2,3,3-hexadeuteriopropoxy)-4-fluorobenzene as a colorless oil (0.98 g). This product is used directly for next step without further purification.

Step 2: A mixture of (6bR,10aS)-1,1-dideuterio-6b,7,8,9,10,10a-hexahydro-1H-pyrido[3',4':4,5]-pyrrolo[1,2,3-de]quinoxalin-2(3H)-one HBr salt (900 mg, 2.9 mmol), 1-(3-bromo-1,1,2,2,3,3-hexadeuteriopropoxy)-4-fluorobenzene (500 mg, 2.1 mmol), and KI (500 mg, 3.6 mmol) in DMF (5 mL) is bubbled with argon for 3 min, and di-isopropyl ethylamine (500 μL, 3.16 mmol) is added. The resulting mixture is heated to 78° C. and stirred at this temperature for 2 h. After cooling to room temperature, the reaction mixture is evaporated to dryness. The residue is suspended in dichloromethane (50 mL), and extracted with water (20 mL). The aqueous phase is separated and extracted with dichloromethane (10 mL). The combined organic phase is dried over Na$_2$CO$_3$ and filtered. The filtrate is concentrated and purified by silica gel column chromatography using a gradient of 0-100% mixed solvents [ethyl acetate/methanol/7N NH$_3$ (10:1:0.1 v/v)] in ethyl acetate to give the title compound as a light brown solid (400 mg, 49% yield). $^1$H NMR (500 MHz, DMSO-d$_6$) δ 10.34 (s, 1H), 7.15-7.05 (m, 2H), 6.93 (ddd, J=6.8, 5.4, 3.3 Hz, 2H), 6.77 (d, J=7.2 Hz, 1H), 6.63 (t, J=7.5 Hz, 1H), 6.58 (d, J=7.2 Hz, 1H), 3.30-3.24 (m, 1H), 3.21 (dt, J=12.9, 6.4 Hz, 1H), 2.85 (dd, J=11.1, 6.4 Hz, 1H), 2.71-2.58 (m, 1H), 2.17-2.04 (m, 1H), 1.94 (d, J=12.7 Hz, 1H), 1.87-1.74 (m, 1H), 1.73-1.62 (m, 1H). MS (ESI) m/z 390.2 [M+1]$^+$.

Example 10: Receptor Binding Activities of Deuterated Compounds

The Compounds of Examples 1, 3, 6, 7, and 9, and the Compound of Formula A, are tested in a radioligand binding assay using human recombinant receptors expressed in either CHO or HEK-293 cell lines. The tested receptors are dopamine $D_1$ receptor (antagonist radioligand), dopamine $D_{2S}$ receptor (agonist radioligand), mu-opioid (MOP) receptor (agonist radioligand), serotonin 5-$HT_{2A}$ receptor (agonist radioligand) and serotonin transporter (SERT) (antagonist radioligand). The binding assays are performed according to the procedures described in the table below:

| Assay | Cell Line | Specific Ligand | Conc. | Kd | Non-Specific Ligand | Incubation | Ref. |
|---|---|---|---|---|---|---|---|
| $D_1$ | CHO | [$^3$H]-SCH 23390 | 0.3 nM | 0.2 nM | SCH 23390 | 60 min, RT | 1 |
| $D_{2S}$ | HEK | [$^3$H]-7-OH-DPAT | 1 nM | 0.68 nM | Butaclamol | 60 min, RT | 2 |
| MOP | HEK | [$^3$H]-DAMGO | 0.5 nM | 0.35 nM | Naloxone | 120 min, RT | 3 |
| 5-$HT_{2A}$ | HEK | [$^{125}$I]-DOI | 0.1 nM | 0.3 nM | DOI | 60 min, RT | 4 |
| SERT | CHO | [$^3$H]-imipramine | 2 nM | 1.7 nM | imipramine | 60 min, RT | 5 |

1. Zhou, Q. Y. et al., *Nature* 347: 76-80 (1990).
2. Grandy, D. K. et al., *Proc. Natl. Acad. Scis. U.S.A.*, 86: 9762-66 (1989).
3. Wang, J. B. et al., *FEBS Lett.*, 338: 217-22 (1994).
4. Bryant, H. U. et al., *Life Sci.*, 15: 1259-68 (1996).
5. Tatsumi, M. et al., *Eur. J. Pharmacol.*, 368: 277-83 (1999).

For all assays performed, the detection method is scintillation counting. The results are expressed as a percentage of control specific binding ([measured specific binding]/[control specific binding]*100) and as a percent inhibition of control specific binding (100−[[([measured specific binding]/[control specific binding]*100]).

The results are shown in the table below:

| Compound | Assay | Test Concentration | % Inhibition (mean) |
|---|---|---|---|
| Ex. 1 | $D_1$ | $1 \times 10^{-7}$M | 36.6 |
| Ex. 6 | $D_1$ | $1 \times 10^{-7}$M | 32.6 |
| Ex. 3 | $D_1$ | $1 \times 10^{-7}$M | 36.3 |
| Ex. 7 | $D_1$ | $1 \times 10^{-7}$M | 34.8 |
| Ex. 9 | $D_1$ | $1 \times 10^{-7}$M | 35.2 |
| Compound A | $D_1$ | $1 \times 10^{-7}$M | 43.4 |
| Ex. 1 | $D_{2S}$ | $3 \times 10^{-7}$M | 47.5 |
| Ex. 6 | $D_{2S}$ | $3 \times 10^{-7}$M | 48.7 |
| Ex. 3 | $D_{2S}$ | $3 \times 10^{-7}$M | 55.1 |
| Ex. 7 | $D_{2S}$ | $3 \times 10^{-7}$M | 53.3 |
| Ex. 9 | $D_{2S}$ | $3 \times 10^{-7}$M | 49.6 |
| Compound A | $D_{2S}$ | $3 \times 10^{-7}$M | 53.6 |
| Ex. 1 | MOP | $2 \times 10^{-8}$M | 47.6 |
| Ex. 6 | MOP | $2 \times 10^{-8}$M | 51.0 |
| Ex. 3 | MOP | $2 \times 10^{-8}$M | 49.1 |
| Ex. 7 | MOP | $2 \times 10^{-8}$M | 59.4 |
| Ex. 9 | MOP | $2 \times 10^{-8}$M | 42.7 |
| Compound A | MOP | $2 \times 10^{-8}$M | 38.9 |
| Ex. 1 | 5-$HT_{2A}$ | $1 \times 10^{-8}$M | 64.7 |
| Ex. 6 | 5-$HT_{2A}$ | $1 \times 10^{-8}$M | 60.2 |
| Ex. 3 | 5-$HT_{2A}$ | $1 \times 10^{-8}$M | 64.1 |
| Ex. 7 | 5-$HT_{2A}$ | $1 \times 10^{-8}$M | 63.5 |
| Ex. 9 | 5-$HT_{2A}$ | $1 \times 10^{-8}$M | 60.1 |
| Compound A | 5-$HT_{2A}$ | $1 \times 10^{-8}$M | 63.0 |
| Ex. 1 | SERT | $1 \times 10^{-6}$M | 34.5 |
| Ex. 6 | SERT | $1 \times 10^{-6}$M | 29.1 |
| Ex. 3 | SERT | $1 \times 10^{-6}$M | 31.8 |
| Ex. 7 | SERT | $1 \times 10^{-6}$M | 31.1 |
| Ex. 9 | SERT | $1 \times 10^{-6}$M | 28.4 |
| Compound A | SERT | $1 \times 10^{-6}$M | 33.4 |

These results demonstrate that the deuterated compounds according to the present disclosure provide comparable in vitro pharmacological potencies with respect to their non-deuterated analog, the Compound of Formula A. However, this data also shows that the pharmacological activity of the deuterated analogs, while similar, is not identical to that of the Compound of Formula A.

Example 11: Pharmacokinetics of Deuterated Compounds

In a first study, the compounds of Examples 2 and 8 are compared to the Compound of Formula A using standard procedures in rats. Each test compound is dissolved in polyethylene glycol 400 vehicle, and administered orally at a dose of 10 mg/kg or subcutaneously at a dose of 3 mg/kg. Plasma concentrations of the drug are measured at time points from 0 to 72 hours post dose. The results are summarized in the table below

| Time (Hr) | PO (ng/mL) Cmpd. A | Ex. 2 | Ex. 8 | SC (ng/mL) Cmpd. A | Ex. 2 | Ex. 8 |
|---|---|---|---|---|---|---|
| 0.033 | 1.0 | 1.0 | 1.3 | 5.7 | 6.0 | 5.7 |
| 0.083 | 10.6 | 10.6 | 8.6 | 26.0 | 27.5 | 25.7 |
| 0.25 | 53.0 | 56.9 | 46.7 | 45.4 | 48.2 | 46.0 |
| 0.5 | 50.4 | 55.7 | 45.8 | 74.1 | 80.0 | 76.4 |
| 1 | 63.2 | 72.3 | 62.4 | 76.4 | 81.4 | 78.9 |
| 2 | 118.1 | 143.3 | 133.2 | 62.0 | 65.2 | 62.9 |
| 6 | 226.0 | 260.5 | 245.2 | 15.3 | 15.0 | 14.1 |
| 8 | 173.8 | 200.0 | 186.8 | 7.8 | 6.7 | 6.5 |
| 12 | 173.3 | 196.4 | 181.1 | 4.2 | 3.9 | 4.1 |
| 24 | 2.5 | 3.0 | 3.3 | 2.1 | 2.1 | 2.1 |
| 48 | BLQ | BLQ | BLQ | 2.1 | 2.0 | 2.4 |
| 72 | BLQ | BLQ | BLQ | 1.1 | 1.0 | 1.4 |
| Tmax (Hr) | 6 | 6 | 6 | 1 | 1 | 1 |
| Cmax (ng/mL) | 78.5 | 64.6 | 68.4 | 76.4 | 81.4 | 78.9 |
| AUC (ng-hr/mL) | 3259 | 3665 | 3387 | 486 | 492 | 494 |

These results show that improved oral pharmacokinetics are observed for the deuterated compounds of Examples 2 and 8 compared to the non-deuterated Compound of Formula A. The total plasma dose obtained (as shown by AUC) is higher for the deuterated compounds, and the plasma concentration of drug during the peak time period from 2 hours to 12 hours post dose show consistently higher levels for the deuterated compounds.

These results further show when dosed subcutaneously-a route that avoids first-pass metabolism in the liver-differences in the plasma concentration profile between the three compounds is significantly attenuated. The deuterated compounds continue to show a slight increase in AUC when administered subcutaneously, but the difference compared to the non-deuterated compound is not significant.

Taking the oral and subcutaneous results together, the data suggests that deuteration limits the extent of first pass hepatic metabolism of the claimed compounds.

What is claimed:

1. A compound of the formula:

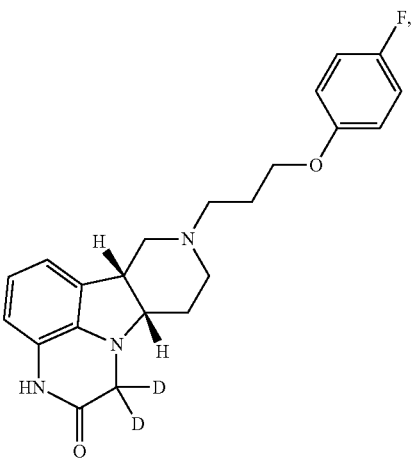 [SMILES: [2H]C1([2H])C(=O)Nc2cccc3c2N1[C@H]1CCN(CCCOc2ccc(F)cc2)C[C@@H]31]

in free or pharmaceutically acceptable salt form.

2. The compound according to claim 1, in the form of a pharmaceutically acceptable salt.

3. The compound according to claim 2, wherein the compound is in the form of an acid addition salt selected from a hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, or isethionic salt.

4. The compound according to claim 1, having greater than 90% incorporation of deuterium at the indicated positions of the structure.

5. A pharmaceutical composition comprising the compound according to claim 1, in free or pharmaceutically acceptable salt form, in admixture with a pharmaceutically acceptable diluent or carrier.

6. The pharmaceutical composition of claim 5, wherein the composition is formulated as a long acting injectable for intramuscular or subcutaneous injection.

7. The compound according to claim 2, wherein the compound is in the form of an acid addition salt selected from a hydrochloric, sulfuric, acetic, succinic, malic, tartaric, citric, ascorbic, glutamic, fumaric, toluenesulfonic, or oxalic salt.

8. The compound according to claim 2, wherein the compound is in the form of an acid addition salt selected from a malic, tartaric, ascorbic, toluenesulfonic, or oxalic salt.

9. The compound according to claim 2, wherein the compound is in the form of an acid addition salt selected from a hydrochloric, malic, tartaric, ascorbic, glutamic, fumaric, toluenesulfonic, or oxalic salt.

10. The compound according to claim 2, wherein the compound is in the form of a toluenesulfonic acid addition salt.

* * * * *